United States Patent
Brueckner et al.

(10) Patent No.: US 10,288,609 B2
(45) Date of Patent: May 14, 2019

(54) SENSITIVITY AND THE DYNAMIC RANGE OF PHOTOMETRIC ASSAYS BY GENERATING MULTIPLE CALIBRATION

(71) Applicant: Roche Diagnostics Operations, Inc., Indianapolis, IN (US)

(72) Inventors: Thorsten Brueckner, Schriesheim (DE); Eloisa Lopez-Calle, Ludwigshafen (DE); Norbert Oranth, Voerstetten (DE); Josef Roedl, Mutterstadt (DE)

(73) Assignee: ROCHE DIAGNOSTICS OPERATIONS, INC., Indianapolis, IN (US)

(*) Notice: Subject to any disclaimer, the term of this patent is extended or adjusted under 35 U.S.C. 154(b) by 0 days.

(21) Appl. No.: 15/951,536

(22) Filed: Apr. 12, 2018

(65) Prior Publication Data

US 2018/0231544 A1     Aug. 16, 2018

Related U.S. Application Data

(63) Continuation of application No. 14/524,633, filed on Oct. 27, 2014, now abandoned, which is a (Continued)

(30) Foreign Application Priority Data

Apr. 26, 2012 (EP) ..................................... 12002952
Dec. 7, 2012 (EP) ..................................... 12196036

(51) Int. Cl.
*G01N 21/27* (2006.01)
*G01N 21/63* (2006.01)
(Continued)

(52) U.S. Cl.
CPC ....... *G01N 33/54393* (2013.01); *G01D 18/00* (2013.01); *G01N 21/274* (2013.01);
(Continued)

(58) Field of Classification Search
CPC .. G01D 18/00; G01N 33/52; G01N 2021/825; G01N 21/274; G06F 19/18; Y02A 90/26
See application file for complete search history.

(56) References Cited

U.S. PATENT DOCUMENTS 4,210,723 A    7/1980 Dorman et al.
5,047,351 A    9/1991 Makiuchi et al.
(Continued)

FOREIGN PATENT DOCUMENTS

EP    0545350    8/1993
EP    0898169    2/1999
(Continued)

OTHER PUBLICATIONS

International Search Report dated Jun. 5, 2013, in Application No. PCT/Ep2013/058675, 3 pages.
(Continued)

*Primary Examiner* — John E Breene
*Assistant Examiner* — Jeffrey P Aiello
(74) *Attorney, Agent, or Firm* — Woodard, Emhardt, Henry, Reeves & Wagner, LLP

(57) ABSTRACT

A method for determining the amount of a specific analyte by photometric assays, wherein the specific analyte in a sample reacts with an analyte specific reaction partner in a reaction mixture. At least two calibration curves are generated, the first calibration curve recorded at a first wavelength is optimized for low concentrations of the specific analyte thereby maximizing the lower detection limit and, the second calibration curve recorded at a second wavelength is optimized for high concentrations of the specific analyte
(Continued)

thereby maximizing the upper detection limit. The optimized lower detection limit and the optimized upper detection limit results in an extended dynamic range.

15 Claims, 9 Drawing Sheets

Related U.S. Application Data continuation of application No. PCT/EP2013/058675, filed on Apr. 25, 2013.

(51) Int. Cl.
<table>
<tr><td>G01N 33/52</td><td>(2006.01)</td></tr>
<tr><td>G06F 19/18</td><td>(2011.01)</td></tr>
<tr><td>G01N 33/543</td><td>(2006.01)</td></tr>
<tr><td>G16B 20/00</td><td>(2019.01)</td></tr>
<tr><td>G01N 21/78</td><td>(2006.01)</td></tr>
<tr><td>G01N 21/82</td><td>(2006.01)</td></tr>
<tr><td>G01D 18/00</td><td>(2006.01)</td></tr>
<tr><td>G01N 33/573</td><td>(2006.01)</td></tr>
<tr><td>G01N 33/68</td><td>(2006.01)</td></tr>
<tr><td>G01N 33/92</td><td>(2006.01)</td></tr>
<tr><td>G16H 50/30</td><td>(2018.01)</td></tr>
</table>

(52) U.S. Cl.
CPC .......... *G01N 21/63* (2013.01); *G01N 21/78* (2013.01); *G01N 21/82* (2013.01); *G01N 33/52* (2013.01); *G01N 33/54313* (2013.01); *G01N 33/54346* (2013.01); *G01N 33/573* (2013.01); *G01N 33/6827* (2013.01); *G01N 33/92* (2013.01); *G16B 20/00* (2019.02); *G16H 50/30* (2018.01); *G01N 2021/825* (2013.01); *Y02A 90/26* (2018.01)

(56) References Cited

U.S. PATENT DOCUMENTS

<table>
<tr><td>5,627,078</td><td>A</td><td>5/1997</td><td>Karl et al.</td><td></td></tr>
<tr><td>6,284,472</td><td>B1</td><td>9/2001</td><td>Wei et al.</td><td></td></tr>
<tr><td>7,449,339</td><td>B2 *</td><td>11/2008</td><td>Samsoondar</td><td>B01L 3/508<br>422/82.05</td></tr>
<tr><td>7,933,014</td><td>B2</td><td>4/2011</td><td>Kanayama et al.</td><td></td></tr>
<tr><td>2003/0059840</td><td>A1</td><td>3/2003</td><td>Chilkoti et al.</td><td></td></tr>
<tr><td>2005/0107956</td><td>A1</td><td>5/2005</td><td>Fukunaga et al.</td><td></td></tr>
<tr><td>2006/0085137</td><td>A1</td><td>4/2006</td><td>Bartkowiak et al.</td><td></td></tr>
<tr><td>2007/0016381</td><td>A1</td><td>1/2007</td><td>Kamath et al.</td><td></td></tr>
<tr><td>2008/0220980</td><td>A1 *</td><td>9/2008</td><td>Lea</td><td>G01N 33/52<br>506/9</td></tr>
<tr><td>2009/0205979</td><td>A1</td><td>8/2009</td><td>Bekki et al.</td><td></td></tr>
<tr><td>2011/0076703</td><td>A1 *</td><td>3/2011</td><td>Borg</td><td>G01N 21/553<br>435/7.93</td></tr>
<tr><td>2012/0316077</td><td>A1 *</td><td>12/2012</td><td>Greef</td><td>G01N 33/54373<br>506/9</td></tr>
<tr><td>2013/0203174</td><td>A1 *</td><td>8/2013</td><td>DiMagno</td><td>G01N 35/00693<br>436/50</td></tr>
<tr><td>2015/0276746</td><td>A1</td><td>10/2015</td><td>Li et al.</td><td></td></tr>
</table>

FOREIGN PATENT DOCUMENTS

<table>
<tr><td>EP</td><td>1460414</td><td>9/2004</td></tr>
<tr><td>EP</td><td>1845373</td><td>10/2007</td></tr>
<tr><td>JP</td><td>S56-168147</td><td>12/1981</td></tr>
<tr><td>JP</td><td>6-94717</td><td>4/1994</td></tr>
<tr><td>JP</td><td>6-109740</td><td>4/1994</td></tr>
<tr><td>JP</td><td>8/75740</td><td>3/1996</td></tr>
<tr><td>JP</td><td>H11-344439</td><td>12/1999</td></tr>
<tr><td>JP</td><td>200-105239</td><td>4/2000</td></tr>
</table>

OTHER PUBLICATIONS

International Preliminary Report on Patentability dated Aug. 12, 2014, in Application No. PCT/EP2013/058675, 16 pages.
Roche Diagnostics Ltd., Cobas 4000 Analyzer Series Freedom to realize your lab's potentail, 2010, 20 pages.
Written Opinion dated May 9, 2014, in Application No. PCT/EP2013/058675, 6 pages.
Alan Kelly et al., A Bichromatic Method for Total Bilirubin with a CentrifiChem 400, Clin Chem, 1979, vol. 25, 1482-1484.
Christopher P. Price, Agglutination Techniques for Detecting Antigen-Antibody Reactions, Encyclopedia of Life Sciences. 2001, 1-7.
D.J. Newman et al., Particle Enhanced Light Scattering Immunoassay, Ann Clin Biochem, 1992, vol. 29, 22-42.
H. Kaiser, Zum Problem der Nachweisgrenze, Fresenius Zeitschrift fur Analytische Chemie, 1965, vol. 209(1), 1-18.
J.A. Molina-Bolivar et al., Latex Immunoagglutination Assays, Journal of Macromolecular Science, Part C—Polymer Reviews, 2005, vol. 45, 59-98.
J.L. Ortega-Vinuesa et al., A Review of Factors Affecting the Performances of Latex Agglutination Tests, J Biomater Sci Polym Ed, 2001, vol. 12 (4), 379-408.
Janice SC Chew et al., Cystatin C-A Paradigm of Evidence Based Laboratory Medicine, Clin Biochem Rev, 2008, vol. 29, 47-62.
Jeffrey S. Jhang et al., Evaluation of Linearity in the Clinical Laboratory, Arch Pathol Lab Med, 2004, vol. 128, 44-48.

* cited by examiner

| Test | Standard conditions [a,c] | | New conditions [a,c] | | Improvement factor: | | |
|---|---|---|---|---|---|---|---|
| | | | Cal 1 | Cal 2 | LDL | LDL | dyn. range |
| CRP: direct assay format with selected MP2 | 570 – 800 nm / 2.0 min | MP1: 110-140 nm, 45mg IgG/g MP2: 220 nm, 50mg IgG/g | 505 – 800 / 2.8 min | 570 – 800 nm / 2.0 min | ∞ | – | ∞ |
| | | | MP1: 110-140 nm, 45mg IgG/g MP2: 290 nm, 60mg IgG/g | MP1: 110-140 nm, 45mg IgG/g MP2: 290 nm, 60mg IgG/g | | | |
| CRP: direct assay format with selected MP1 and MP2 | 570 – 800 nm / 2.0 min | MP1: 110-140 nm, 45mg IgG/g MP2: 220 nm, 50mg IgG/g | 545 – 800 / 7.1 min | 660 – 800 nm / 0.8 min | 3.0 | 2.3 | 6.9 |
| | | | MP1: 90 nm, 50mg IgG/g MP2: 290 nm, 70mg IgG/g | MP1: 90 nm, 50mg IgG/g MP2: 290 nm, 70mg IgG/g | | | |

[a] The CRP L3 assay from Roche includes two different types of particles, large particles MP2 (approx. 220nm) with highly affine anti-CRP antibodies and small particles MP1 (approx. 110-140nm) with less affine anti-CRP antibodies,
[b] Good precision from standard conditions is retained in new conditions,
[c] Main wavelength – correction wavelength / reaction time in minutes

FIG. 2

| Roche test | Standard conditions [d] | New conditions [d] | | Improvement factor [c] | | |
|---|---|---|---|---|---|---|
| | | Cal 1 | Cal 2 | LDL | UDL | dyn range |
| Ferritin Gen. 4 direct assay | 570 – 800 nm / 5.1min | 505 – 800 nm / 4.9min | 570 – 800 nm / 5.1min | 1.7 | - | 1.7 |
| Myoglobin Gen. 2 direct assay | 570 – 800 nm / 4.7min | 505 – 800 nm / 6.7min | 660 – 800 nm / 2.6min | 2 [a] | 2 | 4 |
| D-Dimer Gen. 2 direct assay | 800 nm / 4.3min | 800 nm / 4.3min | 700 nm / 1.4min | - | (1.14) | (1.14) |
| RF II direct assay | 570 – 800 nm / 2.2min | 546 – 800 nm / 8.5min | 660 – 800 nm / 1.4min | 5 [b] | (1.15) | 5.8 |
| CRP L3 (Gen. 3) direct assay | 570 – 800 nm / 2.0min | 505 – 800 nm / 2.0min | 600 – 800 nm / 1.2min | 1.8 | 1.8 | 3.1 |
| DIG competitive assay | 660 nm / 4.7min | 660 nm / 4.7min | 505 – 800 nm / 4.7min | - | (1.15) | (1.15) |
| PHENO competitive assay | 600 – 800 nm / 6.5min | 600 nm / 6.5min | 505 – 800 nm / 7.9min | - | 1.5 | 1.5 |

[a] Without instrument factor; [b] Change calibration to spline; [c] Good precision from standard conditions is retained in new conditions;
[d] Main wavelength – correction wavelength / reaction time in minutes

FIG. 5

|  | for dynamic range based on the invention | Reruns caused by samples below standard measuring range | Reruns caused by samples above standard measuring range |
|---|---|---|---|
| ALTL | 12.2 | 87 % | 99 % |
| ASTL | 7.5 | 87 % | 99 % |
| CRPL3 | 3.1 | 57 % | 99 % |
| D-Dimer Gen.2 | 1.14 | no calculation * | 0 % |
| DIG | 1.15 | 0 % | 27 % |
| Ferritin Gen.4 | 1.7 | 71 % | 0 % |
| GLUC3 | 2.4 | 81 % | 96 % |
| MYO2 | 4 | no calculation * | 51 % |
| PHENO | 1.5 | 3 % | 77 % |
| RF II | 5.8 | 97 % | 9 % |
| U-BUN | 3 | no calculation * | 87 % |

* not enough data available for calculation

FIG. 8

SENSITIVITY AND THE DYNAMIC RANGE OF PHOTOMETRIC ASSAYS BY GENERATING MULTIPLE CALIBRATION

CROSS-REFERENCE TO RELATED APPLICATIONS

This application is a continuation of U.S. patent application Ser. No. 14/524,633, filed 27 Oct. 2014, which is a continuation of International Application No. PCT/EP2013/058675, filed 25 Apr. 2013, which claims the benefit of European Patent Application Nos. 12002952.5, filed 26 Apr. 2012, and 12196036.3, filed 7 Dec. 2012, the disclosures of which are hereby incorporated by reference in their entirety.

BACKGROUND

Agglutination is primarily a chemical phenomenon in which surface interaction between macromolecules leads to crosslinking and the formation of a large complex, resulting in an increase in light scattering. The formation of this large macromolecular complex can be observed using turbidimetric, nephelometric or colorimetric detection.

Turbidimetric, nephelometric and colorimetric assays have the benefits of being quasi-homogeneous assays that do not require any separation or wash step. Due to their easy one-step procedure and their short turn-around times homogeneous immunoassays (HIA) are ideal candidates for the application in automated analyzers. Homogeneous immunoassays are routinely used in the clinical diagnostics for the quantitation of serum proteins, therapeutic drugs and drugs of abuse on clinical chemistry analyzers. So far, the standard method is the use of one main wavelength generating one calibration curve for the determination of analytes in turbidimetric, nephelometric and colorimetric assays.

Although an excellent assay performance can be achieved with HIA on the clinical chemistry analyzers, there are still patient samples with concentrations which are outside of the measuring range. As a consequence the samples have to be re-measured: after dilution in cases where the sample concentration exceeds the upper detection limit, or using higher sample volumes for samples with concentrations below the limit of detection. Re-measurements cause additional expenses and loss of time, both factors being critical for laboratories performing those assays. Therefore, an increase of the dynamic range would reduce the number of reruns.

State-of-the-art methods for addressing these issues are far from optimal—the known methods do not solve the problem of how to proceed with patient samples that are outside of the measuring range especially for automated systems. As a consequence the samples still have to be re-measured: after dilution in cases where the sample concentration exceeds the upper detection limit, or using higher sample volumes for samples with concentrations below the limit of detection. Re-measurements, so-called re-runs, cause additional expenses and loss of time, both factors being critical for laboratories performing those assays.

Furthermore, for several analytes two test systems are available for the measurement of high analyte concentrations and high sensitive test systems for the determination of a low analyte concentration. For example, for the analyte CRP (C-reactive protein) an additional high sensitivity C-reactive (hs-CRP) immunoassay for cardiovascular risk assessment exists (Tina-quant® Cardiac C-reactive protein (Latex) high sensitive (Roche Diagnostics GmbH)) for the determination of low analyte concentration.

As a result, there is a high need for increasing of the sensitivity and extending of the dynamic range in photometric assays.

SUMMARY

It is against the above background that the embodiments of the present disclosure provide certain unobvious advantages and advancements of the prior art. In particular, the inventors have recognized a need for improvements in the sensitivity and the dynamic range of photometric assays.

Although the embodiments of the present disclosure are not limited to specific advantages or functionality, it is noted that the present disclosure provides an improved turbidimetric, nephelometric and colorimetric assay that offers an increased dynamic range and sensitivity. It has now surprisingly be found that the generation of at least two calibration curves in accordance with the present disclosure leads to an improvement of the dynamic range and sensitivity of photometric assays. The present disclosure is expected to (at least partially) overcome the problem of re-measurements of samples.

The present disclosure relates to methods for determining the amount of a specific analyte by photometric assay, wherein the specific analyte in a sample reacts with an analyte specific reaction partner in a reaction mixture. At least two calibration curves are generated; a first calibration curve recorded at a first wavelength is optimized for low concentrations of the specific analyte thereby maximizing the lower detection limit, and a second calibration curve recorded at a second wavelength is optimized for high concentrations of the specific analyte thereby maximizing the upper detection limit.

In case of increasing calibration curves: the optical signal for the specific analyte of a sample to be determined in the reaction mixture is simultaneously measured at least at the first and second wavelength, thereby either the first or the second calibration curve is selected for quantification of the specific analyte. If the optical signal of the first and/or the second wavelength is lower than a corresponding predetermined threshold value, the concentration of the analyte is determined by the use of the first calibration curve recorded at the first wavelength. If the optical signal of the first and/or the second wavelength exceeds a corresponding predetermined threshold value, the concentration of the analyte is determined by the use of the second calibration curve recorded at the second wavelength.

In case of decreasing calibration curves: if the optical signal of the first and/or the second wavelength is lower than a corresponding predetermined threshold value, the concentration of the analyte is determined by the use of the second calibration curve recorded at the second wavelength. If the optical signal of the first and/or the second wavelength exceeds a corresponding predetermined threshold value, the concentration of the analyte is determined by the use of the first calibration curve recorded at the first wavelength. Finally, the amount of the specific analyte is quantified by comparison with the selected calibration curve.

The disclosure especially relates to increasing the sensitivity and/or the dynamic range of photometric assays by using different main wavelengths for determining the amount of a specific analyte by generating at least two calibration curves. Thereby, the first calibration curve records the sensitive detection of the specific analyte, whereas the second calibration curve records the upper measuring range of the specific analyte.

In accordance with one embodiment of the present disclosure, a method for determining the amount of a specific analyte by photometric assays is provided, wherein the specific analyte in a sample reacts with an analyte specific reaction partner in a reaction mixture.

At least two calibration curves are generated; the first calibration curve recorded at a first wavelength is optimized for low concentrations of the specific analyte thereby maximizing the lower detection limit, and the second calibration curve recorded at a second wavelength is optimized for high concentrations of the specific analyte thereby maximizing the upper detection limit.

The optical signal for the specific analyte of a sample to be determined is measured simultaneously in the reaction mixture at least at the first and second wavelengths. Either the first or the second calibration curve is selected for quantification of the specific analyte, by the following criteria:

For increasing calibration curves:
 if the optical signal of the first and/or the second wavelength is lower than a corresponding predetermined threshold value, the concentration of the analyte is determined by the use of the first calibration curve recorded at the first wavelength; or
 if the optical signal of the first and/or the second wavelength exceeds a corresponding predetermined threshold value, the concentration of the analyte is determined by the use of the second calibration curve recorded at the second wavelength.

For decreasing calibration curves:
 if the optical signal of the first and/or the second wavelength is lower than a corresponding predetermined threshold value, the concentration of the analyte is determined by the use of the second calibration curve recorded at the second wavelength; or
 if the optical signal of the first and/or the second wavelength exceeds a corresponding predetermined threshold value, the concentration of the analyte is determined by the use of the first calibration curve recorded at the first wavelength. The amount of the specific analyte is quantified by comparison with the selected calibration curve.

In turbidimetric and nephelometric immunoassays the specific analyte in a sample is quantified from the change in the turbidity of the reaction mixture based on the aggregation of the specific analyte and an analyte specific binding partner, wherein in colorimetric immunoassays the specific analyte in a sample is quantified with the aid of a color reagent.

In accordance with another embodiment of the disclosure, a method for increasing the sensitivity and/or the dynamic range of photometric assays is provided, wherein a first calibration curve recorded at a first wavelength is optimized for low concentrations of the specific analyte thereby maximizing the lower detection limit, and a second calibration curve recorded at a second wavelength is optimized for high concentrations of the specific analyte thereby maximizing the upper detection limit.

In accordance with yet another embodiment of the disclosure, at least two calibration curves are utilized to quantify the amount of a specific analyte of photometric assays, wherein a first calibration curve recorded at a first wavelength is optimized for low concentrations of the specific analyte thereby maximizing the lower detection limit, and a second calibration curve recorded at a second wavelength is optimized for high concentrations of the specific analyte thereby maximizing the upper detection limit.

These and other features and advantages of the embodiments of the present disclosure will be more fully understood from the following detailed description taken together with the accompanying claims. It is noted that the scope of the claims is defined by the recitations therein and not by the specific discussions of features and advantages set forth in the present description.

BRIEF DESCRIPTION OF THE DRAWINGS

The following detailed description of the embodiments of the present disclosure can be best understood when read in conjunction with the following drawings, where like structure is indicated with like reference numerals and in which:

FIG. 2 shows the improvement obtained with an exemplary CRP assay by application of a method in accordance with an embodiment of the present disclosure, in combination with different particle sizes and different antibody loadings of the particles;

FIG. 5 illustrates the improvement/extension of dynamic range that can be achieved without reagent modification when a method, in accordance with an embodiment of the present disclosure, is applied to various commercial assays;

FIG. 8 illustrates various improvements provided by the present disclosure, including an extension of the measuring range of commercially available assays, in accordance with certain embodiments.

DETAILED DESCRIPTION

Figure 1:
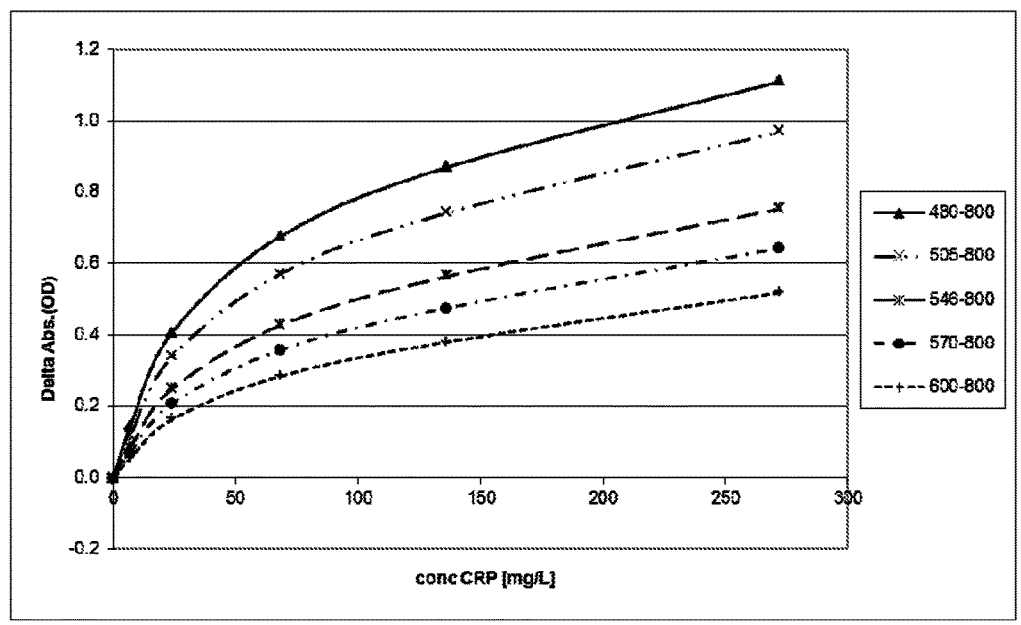
FIG. 1 shows the calibration curves at different wavelengths of an exemplary CRP-assay in accordance with one embodiment of the present disclosure.

In accordance with one embodiment, the present disclosure is directed to a method for determining the amount of a specific analyte by photometric assays, wherein the specific analyte in a sample reacts with an analyte specific reaction partner in a reaction mixture.

At least two calibration curves are generated; the first calibration curve recorded at a first wavelength is optimized for low concentrations of the specific analyte thereby maximizing the lower detection limit, and the second calibration curve recorded at a second wavelength is optimized for high concentrations of the specific analyte thereby maximizing the upper detection limit.

The optical signal for the specific analyte of a sample to be determined is measured simultaneously in the reaction mixture at least at the first and second wavelengths. Either the first or the second calibration curve is selected for quantification of the specific analyte, by the following criteria for increasing calibration curves:

For increasing calibration curves:
- if the optical signal of the first and/or the second wavelength is lower than a corresponding predetermined threshold value, the concentration of the analyte is determined by the use of the first calibration curve recorded at the first wavelength; or
- if the at least one optical signal of the first and/or the second wavelength exceeds a corresponding predetermined threshold value, the concentration of the analyte is determined by the use of the second calibration curve recorded at the second wavelength.

For decreasing calibration curves:
- if the optical signal of the first and/or the second wavelength is lower than a corresponding predetermined threshold value, the concentration of the analyte is determined by the use of the second calibration curve recorded at the second wavelength; or
- if the optical signal of the first and/or the second wavelength exceeds a corresponding predetermined threshold value, the concentration of the analyte is determined by the use of the first calibration curve recorded at the first wavelength. The amount of the specific analyte is quantified by comparison with the selected calibration curve.

In accordance with the present disclosure, it was surprisingly found that the simultaneous measurement of a specific analyte at two different wavelengths and different reaction times generating at least two calibration curves from one run (one measurement) increases the dynamic range of photometric assays.

Photometric assays encompass turbidimetric and nephelometric immunoassays as well as colorimetric assays. In turbidimetric and nephelometric immunoassays the specific analyte is quantified from the change in the turbidity of the reaction mixture based on the agglutination of the specific analyte and an analyte specific binding partner, while in colorimetric assays the specific analyte is quantified with the aid of a color reagent.

The measurement at a first in most instances short wavelength at a first reaction time allows an optimal detection with respect to sensitivity, and the parallel measurement at a second in most instances larger wavelength at a second reaction time ensures a high upper detection limit, both resulting in an extended dynamic range compared to the measurement at only one wavelength at one reaction time. As a consequence, an extension of the dynamic range is achieved without the need to modify the assay reagents and their formulations, thus ensuring a fast and cost-effective realization. Subsequently, depending upon the signal value obtained for a sample, a suitable calibration curve is used for the quantification of the specific analyte. It is now possible to increase the dynamic range of the assay in comparison to standard techniques.

In accordance with another embodiment of the present disclosure, there are cases where a large wavelength at a first reaction time allows an optimal detection with respect to sensitivity, and the parallel measurement at a second smaller wavelength at a second reaction time ensures a high upper detection limit, both resulting in an extended dynamic range compared to the measurement at only one wavelength at one reaction time.

When performing an agglutination assay in the competitive inhibition format the measurement at a first in most instances larger wavelength at a first reaction time allows an optimal detection with respect to sensitivity, and the parallel measurement at a second in most instances shorter wavelength at a second reaction time ensures a high upper detection limit, both resulting in an extended dynamic range compared to the measurement at only one wavelength at one reaction time.

In accordance with yet another embodiment of the present disclosure, there are cases where a small wavelength at a first reaction time allows an optimal detection with respect to sensitivity, and the parallel measurement at a second larger wavelength at a second reaction time ensures a high upper detection limit, both resulting in an extended dynamic range compared to the measurement at only one wavelength at one reaction time.

The term "determining" as used herein means assessing, diagnosing, deciding, identifying, evaluating, or classifying whether a specific analyte in a sample is quantified from the change in the turbidity of the reaction mixture based on the agglutination of the specific analyte and an analyte specific binding partner by turbidimetric and nephelometric immunoassays or whether the specific analyte is quantified with the aid of a color reagent in colorimetric assays.

The term "amount" as used herein is encompasses the absolute amount of an analyte or the relative amount and/or concentration of said analyte and/or any value and/or parameter which may correlate thereto and/or may be derived therefore.

The term "sample" as used herein is refers to a sample of a body fluid selected from blood, i.e., whole blood, plasma, or serum, or urine, CSF, sputum or to a sample of separated cells or to a sample from a tissue or an organ of a respective individual. Samples of body fluids can be isolated by well-known techniques. Tissue or organ samples may be isolated from any tissue or organ by, e.g., biopsy. Separated cells may be isolated from the body fluids or the tissues or organs by separating techniques such as centrifugation or cell sorting. Typically, lysates from cell-, tissue- or organ samples are isolated from those cells, tissues or organs which express or produce the peptides referred to herein.

The term "agglutination" as used herein is primarily a chemical phenomenon in which surface interaction between macromolecule leads to crosslinking and to the formation of a large complex. The formation of this large complex leads to an increase in light-scattering properties that, depending on the size of the complex, can be observed with the naked eye or monitored photometrically using turbidimetric and nephelometric detection (see Christopher P. Price, Encyclopedia of Life Sciences 2001, p. 1-7).

The assay method of the present disclosure can be any type of light scattering assay, in particular turbidimetric, nephelometric and colorimetric assays. The assay can be used for determining the amount of any specific analyte suitable to be determined by turbidimetric, nephelometric and colorimetric assays, i.e., any analyte for which there are reaction partners apt to be bound that specifically recognize the analyte.

The term "turbidimetry and nephelometry" are methods known in the art for determining the amount of cloudiness, or turbidity, in a solution based upon measurement of the effect of this turbidity upon the transmission and scattering of light. Turbidity in a liquid is caused by the presence of finely divided suspended particles. If a beam of light is passed through a turbid sample, its intensity is reduced by scattering, and the quantity of light scattered is dependent upon the concentration and size distribution of the particles. The spectrophotometer measures the increased turbidity (i.e., the reduction of light in the intensity transmitted light), which is due to the increasing particle size resulting from the immunoagglutination reaction. This increased turbidity is a direct measure of the immunoagglutination caused by the analyte or an indirect measure of the immunoagglutination inhibition caused by the analyte. In nephelometry, the intensity of the scattered light is measured, while in turbidimetry, the intensity of light transmitted through the sample is measured.

Turbidimetric assays involve measurement of the intensity of the incident beam as it passes through the sample. The light beam may pass through a suspension or be absorbed, reflected, or scattered by the particles. As a consequence, the intensity of light decreases as it is transmitted through the suspension. For nonabsorbing particles the decrease in light intensity due to scattering is expressed as turbidity.

Nephelometric assays refer to the measurement of the light scattered at an defined angle of 0 from the incident beam when the incident beam is passed through the sample. In nephelometry the change in the intensity of the scattered light after a time is measured because the scattering species rapidly increase size. The scattered light is proportional to the initial antigen concentrations when measured in the presence of a fixed antibody-latex complex. Further explanations are described by J. A. Molina-Bolivar et al., Journal of Macromolecular Science, Part C-Polymer Review, 45:59-98, 2005.

The immunoassay method of the present disclosure works with all known agglutination tests with and without microparticle enhancement.

Typically used within the present disclosure are "microparticle-enhanced light scattering agglutination tests" which is also called "particle-enhanced turbidimetric immunoassays" (PETIA). Particle-enhanced immunoassays are routinely used in clinical diagnostics for the quantitation of serum proteins, therapeutic drugs and drugs of abuse on clinical chemistry analyzers, because they have the benefits of being quasi-homogeneous assays that do not require any separation or wash step. To enhance the optical detection between the specific analyte and an analyte specific binding partner in the reaction mixture, the analyte or the analyte specific binding partner is linked to suitable particles. Thereby, the analyte reacts and agglutinates with the particles that are coated with analyte specific binding partners. With increasing amount of analyte, the agglutination and the size of the complexes are increasing, leading further to a change of light scattering. The agglutinated particles are determined by turbidimetric and nephelometric measurements.

The material of the microparticles may be any inorganic, organic, or polymer material suitable for microparticle enhanced light scattering assays. Such materials include, for example, selenium, carbon, gold; nitrides of carbon, silicium or germanium, e.g., $Si_3N_4$; oxides of iron, titanium or silicium, e.g., $TiO_2$ or $SiO_2$; and polymeric materials such as, for example, polystyrene, poly(vinyl chloride), epoxy resins, poly(vinylidene chloride), poly(alphanaphtyl methacrylate), poly(vinylnaphthalene), or copolymers thereof, in particular copolymers of styrene and a copolymerizable ethylenically unsaturated compound, e.g., styrene-(meth) acrylate co-polymers. Microparticles made of polymeric materials, as well as core-shell particles consisting of an inner core polymerized from styrene and an outer shell formed by copolymerization from styrene with a copolymerizable ethylenically unsaturated compound, as described, e.g., in U.S. Pat. No. 4,210,723, are particularly suitable. The majority of particle based assays employ latex particles, with the predominant type being of polystyrene. A review of latex agglutination tests is described in J. L. Ortega-Vinuesa, J. Biomater. Sci. Polymer Edn, Vol. 12, No. 4 pp. 379-408 (2001).

There are different test formats for particle-enhanced turbidimetric immunoassays (PETIA); the competitive format and the direct format.

The direct format is preferably applied for analytes having a large size. These analytes are polyvalent antigens with multiple epitopes, e.g., proteins and microorganisms. For the direct format the particles are coated with antibodies that agglutinate with the analyte.

Turbidimetric and nephelometric assays may also be performed in a competitive inhibition format. This format is used most often to measure small molecules, such as haptens, and is usually applied in diagnostics for drugs of abuse testing and therapeutic drug monitoring. In this format the assay reagent not only contains an analyte specific binding partner, but also a chemically modified analyte obtained by attaching it to a microsphere surface or to another carrier molecule, such as a protein (e.g., bovine serum albumin) or a soluble polymer or oligomer. In contrast to the unmodified analyte, this reagent is able to agglutinate in the presence of an analyte specific binding partner due to the multiple copies of analyte present in the molecule. The analyte in a sample is quantified from the change in the turbidity of the reaction mixture based on the aggregation of the specific analyte and an analyte specific binding partner in the presence of the modified analyte.

The antigens are linked to a cross-linking agent, e.g., polyhaptens, which competes against the antigen of the sample for the binding site of the antibody as shown in European Patent No. 0 545 350 B1. Here a soluble polymer, a protein or a microparticle acts as carrier molecule for multiple copies of the antigen. The amount of unlabeled antigen in the test sample is measured by its ability to compete with labeled antigen in the immunoassay. The unlabeled antigen blocks the ability of the labeled antigen to bind because that binding site on the antibody is already occupied. Thus, in a competitive immunoassay, less label measured in the assay means more of the unlabeled (test sample) antigens is present.

Typically used is a microparticle enhanced light scattering agglutination assay for determining the amount of an analyte that comprises using a mixture of particles of strong light scattering properties carrying at least one binding partner of high reactivity for the analyte and particles of weak light scattering properties carrying at least one binding partner of low reactivity for the analyte as described in European Patent No. 0 898 169 B1. The particles of strong light scattering properties have a larger size and/or a higher refractive index than the particles of weak light scattering properties. The microparticle reagent for a microparticle enhanced light scattering immunoassay for determining the amount of an analyte, which comprises a mixture of microparticles of 30 to 600 nm in diameter, including particles of strong light scattering properties carrying at least one binding partner of high reactivity partner for the analyte and particles of weak light scattering properties carrying at least one binding partner of low reactivity for the analyte. The microparticles are usually approximately spherical with a narrow size distribution, a good representation of their size being their mean diameter. According to the law of light scattering (D: J. Newman et al., 1992, Ann. Clin. Biochem. 29, 22-42) strong light scattering properties result from a large particle size and/or a high ratio of the refractive index of the particle to that of the medium, whereas weak light scattering result from a small particle size and/or a low ratio of the refractive index of the particle to that of the medium.

The term "spectrophotometric assay", also called "photometric assay", is well known in the art. Photometric assays encompass turbidimetric and nephelometric immunoassays as well as colorimetric assays. In turbidimetric and nephelometric immunoassays the specific analyte is quantified from the change in the turbidity of the reaction mixture based on the agglutination of the specific analyte and an analyte specific binding partner, while in colorimetric assays the specific analyte is quantified with the aid of a color reagent. In spectrophotometric assays, the course of the reaction is followed by measuring a change in how much light the assay solution absorbs. If this light is in the visible region you can actually see a change in the color of the assay, these are called colorimetric assays. The MTT assay, a redox assay using a tetrazolium dye as substrate is an example of a colorimetric assay. UV light is often used, since the common coenzymes NADH and NADPH absorb UV light in their reduced forms, but do not in their oxidized forms. An oxidoreductase using NADH as a substrate could therefore be assayed by following the decrease in UV absorbance at a wavelength of 340 nm as it consumes the coenzyme.

Even when the enzyme reaction does not result in a change in the absorbance of light, it can still be possible to use a spectrophotometric assay for the enzyme by using a coupled assay. Here, the product of one reaction is used as the substrate of another, easily detectable reaction. An example for a coupled assay is the enzyme hexokinase, which can be assayed by coupling its production of glucose-6-phosphate to NADPH production, using glucose-6-phosphate dehydrogenase.

The term "colorimetric assays" according to the present disclosure are routinely used in the clinical diagnostics on highly automated clinical chemistry analyzers. Due to their easy one-step procedure and their short turn-around times, homogeneous colorimetric assays are ideal candidates for the application in automated analyzers. A broad test menu for the clinical chemistry analyzers are actually offered, e.g., COBAS C (Roche Diagnostics GmbH). Colorimetric assays are characterized by formation or change or the depletion of the color in the presence of the analyte to be quantified. Typical colorimetric tests running on lab analyzers are the clinical chemistry tests and enzyme-immuno tests (CEDIA, EMIT). Such assays are detected by spectrophotometry in spectrometers. The detection of these assays on Roche COBAS C instruments is based on a photometer with a tungsten halogen lamp as irradiation source and photodiode array (12 diodes yielding 12 wavelengths between 340 and 800 nm) as detector. The O.D. is directly proportional to the concentration of the colored compound. If the development of color is linked to the concentration of a substance in solution, the concentration can be measured by determining the extent of absorption of light at the appropriate wavelength. In accordance with one embodiment of the present disclosure, a method is provided wherein in colorimetric immunoassays the specific analyte is quantified with the aid of a color reagent.

The term "color reagent" encompasses any assay reagent or a mixture of assay reagents that lead to a color change, color formation or color depletion of the assay, which can be measured on the photometer with typical wavelengths ranging from 340 to 800 nm. Many colorimetric assays involve an enzyme and the corresponding substrate that lead to colored products in a one- or more-step-reaction; the color change may be induced by corresponding enzymatic cofactors like NAD/NADH rather than by the substrate itself. There are also colorimetric assays based on the specific reaction of the analyte with a chemical reagent that leads to a colored product in a one or more step-reaction. In colorimetric immunoassays like EMIT or CEDIA the color is typically formed by the reaction of a reporter enzyme, like ß-galactosidase or a dehydrogenase, with its corresponding substrate leading to a product with characteristic and detectable absorption properties. The reaction of the reporter enzyme with the substrate typically takes place after the immunoreaction between analyte and antibody, which then triggers or inhibits the enzymatic reaction. In other colorimetric tests, like typical clinical chemistry tests for lab analyzers, the color is formed, changed or depleted by the reaction of the analyte with enzymes or any other specific chemical reagent or a combination thereof. In some cases the analyte itself acts as enzyme. Even when the enzyme reaction does not result in a change in the absorbance of light, it can still be possible to use a spectrophotometric assay for the enzyme by using a coupled assay. Here, the product of one reaction is used as the substrate of another, easily detectable reaction. An example for a coupled assay is the enzyme hexokinase, which can be assayed by coupling its production of glucose-6-phosphate to NADPH production, using glucose-6-phosphate dehydrogenase.

The term "Rayleigh scattering" is the elastic scattering of light or other electromagnetic radiation by particles much smaller than the wavelength of the light. The particles may be individual atoms or molecules. It can occur when light travels through transparent solids and liquids, but is most prominently seen in gases. Rayleigh scattering is a function of the electric polarizability of the particles. Scattering by particles similar to or larger than the wavelength of light is typically treated by the Mie theory, the discrete dipole approximation and other computational techniques. Rayleigh scattering applies to particles that are small with respect to wavelengths of light, and that are optically "soft" (i.e., with a refractive index close to 1). The amount of Rayleigh scattering that occurs for a beam of light depends upon the size of the particles and the wavelength of the light.

The term "analyte" according to the present disclosure encompasses any "in vitro diagnostic compound" such as, e.g., serum proteins, therapeutic drugs and drugs of abuse. Representative analytes include, but are not limited to, antigens, haptens, antibodies, proteins, peptides, amino acids, hormones, steroids, cancer cell markers, tissue cells, viruses, vitamins, nucleic acids, and pesticides. As used herein, an "analyte" or "specific analyte" refers to the substance whose presence and/or concentration in a sample is to be determined. The term "analyte" includes any substance for which there exists a specific reaction partner (e.g., a binding molecule or substance which specifically binds the analyte), or for which a specific binding partner can be prepared.

Analytes that can be determined by the assay of the present disclosure include antigenic analyte, the binding partner then suitably being immunological binding partners. The antigenic analytes may be monomeric or polymeric, with or without repetitive epitopes.

Suitable antigenic analytes include:
  a) Specific proteins such as, e.g., alpha-1-acid glycoprotein (AAGP), alpha-1-antitrypsin (AAT), albumin in serum (ALBS), microalbumin (ALBU), apolipoprotein A-1 (APOA), apolipoprotein B (APOB), antistreptolysin O (ASO), antitrombin III (AT III), complement C3c (C3C), complement C4 (C4), C-reactive Protein (CRP), fibrinogen (FIBG), fibronectin (FIBR), haptoglobulin (HAPT), immunglobulin A, G, M (IgA, IgG, IgM), lipoprotein a (LPA), rheumatoid factors (RF), transferrin (TRSF), serum amyloid A (SAA);

b) Tumor markers such as, e.g., alpha-fetoprotein (AFP), human chorionic gonadotropin beta-subunit (b-HCG), beta-2-microglobulin, carbohydrate antigens such as CA 125, CA 15-3, CA 19-9, CA 72-4, carcinoembryonic antigen (CEA), ferritin, mucin-like carcinoma associated antigen (MCA), neuron specific enolase (NSE), prostate specific antigen (PSA);

c) Cardiovascular or fibrinolysis markers such as, e.g., fatty acid binding protein (FABP), fibrin and fibrinogen degradation products (FDP), FDP D-dimer, troponin, myoglobin, glycated hemoglobin A1c (HbA1c);

d) Virus markers such as, e.g., influenza virus, Herpes simplex virus (HSV);

e) Immunoglobin E (IgE), Insulin, Cystatin C;

f) Immunosuppressives such as, e.g., Cyclosporine, Everolimus, MPA (Mycophenolic Acid), Sirolimus, Tacrolimus;

g) Therapeutic drugs such as, e.g., Acetaminophen, Aminoglycosides, Amphetamines, Amikacin, Barbiturate, Benzodiazepines, Buprenorphine, Carbamazepine, Cocaine, Digoxin, Digitoxin, Ecstasy, Gentamicin, HIV Protease Inhibitors, Lidcaine, LSD, MDEA, Methadone, Methamphetamine, Methaqualone, 6-Monoacetyl-morphine, Napa, Procainamide, Phenytoin, Phencyclidine, Phenobarbital, Propoxyphene, Quinidine, Salicylate, Theophylline, THC, Tricyclic Antidepressants, Tobramycin, Vancomycin, VPA Analytes that can be determined by the assay of the present disclosure further include nucleic acids, the binding partners then suitably being oligonucleotide capture probes showing sufficient sequence complementarity for hybridization to take place. Suitable nucleic acid analytes include DNA, RNA and derivatives thereof, the determination of the amount of which is of interest in the diagnostic or pharmaceutical field. Examples of such nucleic acids that be quantitatively determined using the assay of the present disclosure are HIV1-RNA, HIV2-RNA, HCV-RNA, enterovirus RNA, HTLV-DNA, CMV-DNA and *Mycobacterium tuberculosis* DNA.

As an example, the analytes CRP (C-reactive protein), Ferritin, Myoglobin, D-Dimer, RF II (Rheuma-factor II), DIG (Digoxin) and Phenobarbital were determined in a sample according to the methods of the present disclosure.

The term "analyte specific reaction partner" as used herein is able to react with the specific analyte so as to form a reaction complex, like an antigen-antibody immunocomplex, or to form a new product, like the product resulting from an enzyme-substrate reaction. Typical analyte specific reaction partners include, but are not limited to, binding proteins, antigens, antigen fragments, antibodies, antibody fragments, nucleic acids, receptors and particle enhanced binding partners, enzymes, substrates (in cases where the analyte is an enzyme), and specific chemical reagents leading to a color change in the presence of analyte. Such reaction partners specific for a given analyte may be obtained from commercial sources or may be prepared in accordance with standard procedures known to those skilled in the art. Examples of analyte specific reaction partner pairs include, but are not limited to, hapten:antibody, biotin:avidin, hormone:receptor, polypeptide:antibody, and oligonucleotide:complementary DNA or RNA, enzyme-substrate. For analyte specific reaction partners leading to the formation of a binding complex with the analyte, as it is the case with antibodies, the term "analyte specific binding partner" can equally be used instead of "analyte specific reaction partner".

The term "antibody" as used herein refers to immunoglobulins that are produced in response to the detection of a foreign substance, and includes intact molecules as well as functional fragments thereof, such as, Fab, F(ab')2, and Fv. Antibodies that can be used as immunological binding partners in the assay of the present disclosure include polyclonal antibodies of any species, monoclonal antibodies of any species (including chimeric antibodies and/or recombinant antibodies). Because of their capacity of being produced identically in unlimited amounts, monoclonal antibodies or fragments thereof are generally preferred.

The term "antigen" as used herein is characterized by its ability to be bound at the antigen-binding site of an antibody. The region of an antigen that is recognized by an antibody, and to which the antibody binds, is referred to as an "epitope." An antigen is a substance that is capable of inducing an immune response, i.e., antibody production, when introduced into an animal or human body. A hapten is a small molecule that can elicit an immune response only when attached to a large carrier such as a protein. The carrier may be one that also does not elicit an immune response by itself. Once the body has generated antibodies to a hapten-carrier adduct, the small-molecule hapten may also be able to bind to the antibody.

It is common practice to determine the concentration of an analyte by using a "calibration curve" (also commonly referred to as standard curve or working curve), which has been preliminarily drawn by plotting the interrelation between the known concentrations of the analyte in the standard samples and the analytical measured values such as optical densities of the standard samples. When the calibration curve has an adequate linearity over a wider range in the region of quantitative analysis, the calibration curve can be prepared with a relatively smaller number of standard samples, which are near the upper limit, lower limit and in the intermediate point in the determination range of the quantitative analysis.

In practice, however, there are many calibration curves that are not linear in general. The calibration curve of turbidimetric, nephelometric or colorimetric assays, prepared from the absorbance of a specific wavelength, typically is a nonlinear S-shape calibration curve where the sensitivity is deteriorated at the concentration near zero, and is saturated at a higher concentration side. The determination of the S-shape calibration requires a multipoint calibration where the use of the standard samples of the plurality of the concentrations is obliged.

Furthermore, this S-shape calibration curve lacks of reportable measuring range at very low and at very high concentrations. Although several methods exist there are still patient samples with concentrations that are outside of the measuring range. As a consequence the samples have to be diluted in cases where the sample concentration exceeds the upper detection limit, or a higher volume of the samples have to be used for samples with concentrations below the limit of detection. These re-measurements, so-called re-runs, cause additional expenses and loss of time, both factors being critical for laboratories performing those assays. To avoid these disadvantages new methods are provided herein for increasing the sensitivity and extending the dynamic range of turbidimetric, nephelometric or colorimetric assays.

When generating a calibration curve for an agglutination assay based on measurements of the turbidity of the reaction mixture, the selection of the wavelength plays, beside the reaction time, a crucial role for the slope (analytical sensitivity) of the curve and the achievable upper measuring range. For the direct assay format small wavelengths may lead to calibration curves with high slopes and high signals, whereas for the high concentration region the curves may become early a flat leading to comparable signal values for high concentrations and in consequence also to low upper detection limits. On the other hand larger wavelengths may lead to curves with small slopes but to distinguishable signal values for the high concentration region. The selection of the one wavelength and a corresponding reaction time for the signal calculation aimed at the generation of a calibration curve may therefore be a compromise between analytical sensitivity and upper measuring range. Similar situation is encountered in colorimetric assays. The selection of a wavelength near to the absorption maximum of the formed colored product ensures a high signal and high sensitivity, on the other hand the signals for high analyte concentrations may be outside of the specified optical range of the detector.

In an embodiment of the present disclosure, two calibration curves are simultaneously generated for two different wavelengths and reaction times, which surprisingly allow the quantification of a specific analyte in a sample with an increased dynamic range. For this purpose the sample is also measured using at least these two different wavelengths and reaction times. At least one optical signal of the sample or at least one signal value calculated hereof decides which calibration curve is to be used for its quantitation.

The term "first calibration curve" as used herein is generated from the optical signals of the reaction mixture at a first wavelength and a first reaction time, both optimized for achieving a low detection limit. The first calibration curve recorded at a first wavelength and a first reaction time is optimized for low concentrations of the specific analyte thereby maximizing the lower detection limit.

The term "second calibration curve" as used herein is generated from the optical signals of the reaction mixture at a second wavelength and a second reaction time, both optimized for achieving a high upper detection limit. The second calibration curve recorded at a second wavelength and a second reaction time is optimized for high concentrations of the specific analyte thereby maximizing the upper detection limit. Working with two instead with one calibration curve as it is done in the present disclosure may also show further benefits such as to alleviate issues related to the number and concentrations of required calibrators as well as the curve-fitting procedure for the calibration curve. The calibration curves that are generated in accordance with the present disclosure are predetermined for the specific analyte by using a standard sample.

After preparing the measuring sample by mixing the sample with the analyte specific reaction partner and the analyte, which may be chemically modified, the reaction mixture is allowed to react for a given complete reaction time. The optical signal for the specific analyte of the sample to be determined in the reaction mixture is measured simultaneously at least at the first and second wavelengths over the complete reaction time.

Either the first or the second calibration curve, recorded at the first wavelength and a first reaction time, or recorded at the second wavelength and second reaction time, respectively, is selected for quantification of the specific analyte, wherein based on at least one of the optical signals of the sample or based on at least one signal value calculated hereof either the first or the second calibration curve is selected for the calculation of the analyte concentration, by the following criteria:

For increasing calibration curves:
If the optical signal of the first and/or the second wavelength is lower than a corresponding predetermined threshold value, the concentration of the analyte is determined by the use of the first calibration curve recorded at the first wavelength and a first reaction time;
If at least one optical signal of the first and/or the second wavelength exceeds a corresponding predetermined threshold value, the concentration of the analyte is determined by the use of the second calibration curve recorded at the second wavelength and second reaction time.

For decreasing calibration curves:
If the optical signal of the first and/or the second wavelength is lower than a corresponding predetermined threshold value, the concentration of the analyte is determined by the use of the second calibration curve recorded at the second wavelength and second reaction time;
If the optical signal of the first and/or the second wavelength exceeds a corresponding predetermined threshold value, the concentration of the analyte is determined by the use of the first calibration curve recorded at the first wavelength and first reaction time. The amount of the specific analyte is quantified by comparison with the selected calibration curve.

The present disclosure provides a method for determining the amount of a specific analyte by photometric assays, wherein the specific analyte in a sample reacts with an analyte specific reaction partner in a reaction mixture. Depending on the spectrophotometer and the available wavelengths at least two calibration curves for a first and a second wavelengths at a first and second reaction time are generated, which were predetermined for the specific analyte. Thereby the optical signal for the specific analyte of a sample to be determined is measured simultaneously in the reaction mixture at the first and second wavelengths.

The terms "first wavelength" and "first reaction time" as used herein are optimized for low concentrations of the specific analyte thereby maximizing the lower detection limit. That means the first wavelength in combination with the first reaction time generates, e.g., high signals in case of the direct assay format, leading to a calibration curve that has a high analytical sensitivity. Sensitivity, analytical sensitivity, lower detection limit (LDL), limit of blank (LOB), limit of detection (LOD) and limit of quantitation (LOQ) are terms used to describe the smallest concentration of a measurand that can be reliably measured by an analytical method. All of these terms are related but have distinct definitions (siehe Lit. din biochem rev 2008, 29, 49). For example, the term "analytical sensitivity" is defined as the slope of the calibration curve.

The term "lower detection limit" (LDL) as used herein is also called lower measuring range. A typical approach to estimate the LDL consists of measuring replicates, such as n=21, of a zero calibrator or blank sample, determining the mean value x and standard deviation (SD). The LDL is calculated as x+2SD or x+3SD. This method for the LDL determination is according to the method described by Kaiser (H. Kaiser, Fresenius Zeitschrift für analytische Chemie, 1965, 209, Nr. 1, pages 1-18). If the least one optical signal of a sample (out of the optical signals of the sample simultaneously measured at least at the first and second wavelengths over the complete reaction time) or the at least one signal value calculated hereof is lower than a corresponding predetermined threshold value, the concentration of the analyte is determined by comparison with the calibration curve of the first wavelength and the first reaction time for assays with increasing calibration curves. In case of competitive agglutination assays or in case of colorimetric assay with falling calibration curves, the calibration curve of the second wavelength and the second reaction time would be used, if the least one optical signal of a sample (out of the optical signals of the sample simultaneously measured at least at the first and second wavelengths over the complete reaction time) or the at least one signal value calculated hereof is lower than a corresponding predetermined threshold value.

The terms "second wavelength" and "second reaction time" as used herein is optimized for high concentrations of the specific analyte thereby maximizing the upper detection limit. That means the second wavelength and the second reaction time generates, e.g., distinguishable signals for different analyte concentrations in the upper measuring range in case of the direct assay format leading to a calibration curve with a high upper measuring range.

The first and second wavelengths are different, ideally by at least 5 nm, while the first and second reaction times may be different or identical.

The term "upper detection limit" (UDL) as used herein is also called the upper measuring range. The UDL is the highest amount of the analyte in a sample that can reliably be determined. In accordance with an embodiment of the present disclosure, the UDL was determined by evaluating the linearity of the method and then selecting the highest concentration value within the linear range as the UDL. The method is said to be linear when the analyte recovery from a series of sample solutions (measured value) is proportional to the actual concentration of the analyte (true value) in the sample solutions (Arch Pathol Lab Med 2004, 128, pages 44-48). The form of the calibration curve, which can be parabolic or sigmoid-shaped, should not be confused with the linearity of the method which describes the relationship between the measured value and the true value. The calibration curve describes the relationship between signal and concentration.

The term "dynamic range" in the context of the present disclosure describes the magnitude of the measuring range of an assay and is here defined as ratio of upper detection limit (UDL) to lower detection limit (LDL). If not indicated otherwise we use the term measuring range as concentration values starting at the LDL and ending at the UDL. Principally other sensitivity terms may be used than the LDL, like LOD or LOQ, and also other terms describing the upper measuring range than the UDL may be used to calculate the dynamic range.

Both wavelengths, the first and the second wavelength, are the so called "main wavelengths" according to the state of the art for measuring the analyte.

The term "optical signal" as used herein describes the signal that is obtained by performing a absorbance measurement of the reaction mixture. The optical signal may be an absorbance value in case of turbidimetric and colorimetric assays or a scattered light signal for nephelometric assays.

The term "signal value calculated hereof" in the context of the present disclosure means a change of the optical signal of the reaction mixture, and may be the difference between two absorbance measurements, an initial and a final measurement, or may be a kinetic parameter expressing the absorbance change per time. Usually, the initial measurement may be performed before or shortly after the final reagent is added to the reaction mixture.

The term "reaction time" as used herein is the time period between the first (or initial) and second (or final) measurement of the optical signal that is used for the calculation of a signal value hereof. The first (or initial) measurement is performed before or shortly after the final reagent is added to the reaction mixture. In case of kinetic measurements the reaction time may be the time period used for the calculation of the value expressing the absorbance change per time. The "reaction time" may be identical or shorter that the "complete reaction time".

The term "specific analyte" in the context of the present disclosure means that for each analyte in a sample to be measured, specific calibration curves and specific wavelengths and reaction times may be determined that are optimized for each specific analyte to quantify the concentration, and which may differ from analyte to analyte. Common photometers are spectrophotometers or turbidimeters for turbidimetric immunoassays, and nephelometers for nephelometric immunoassays. A multiple wavelength spectrophotometer known in the art is used for measuring the optical signal for the specific analyte of a sample to be determined in the reaction mixture according to the present disclosure. Typically used for colorimetric assays and turbidimetric and nephelometric immunoassays is a spectrophotometer.

Depending on the architecture of the chosen spectrophotometer and the available wavelengths, which may differ from device to device, a first and a second wavelength is selected out of multiple wavelengths. The photometer as used herein is the Roche COBAS C 311 analyzer (Roche Diagnostics GmbH) having the ability to measure 12 wavelengths between 300 nm to 800±2 nm simultaneously. Typically used are the wavelengths 340, 376, 415, 450, 480, 505, 546, 570, 600, 660, 700, 800±2 nm. The method of the present disclosure is especially advantageous if used in automated analyzers, such as the Roche COBAS C 311, having the capability of measuring multiple wavelengths simultaneously. The measurements are typically performed at a defined temperature, typically between 20 and 40 degrees Celsius.

As an example, the first and second wavelengths and the first and second reaction times for the generation of the first and second calibration curves aimed at the quantification of several specific analytes were determined according to the present disclosure on a Roche COBAS C 311 analyzer under standard conditions. The instrument automatically pipettes the sample and the assay reagents into reaction cells (=cuvette). The instrument measures the absorbance simultaneously at 12 different wavelengths: 340, 376, 415, 450, 480, 505, 546, 570, 600, 660, 700, 800±2 nm. For each reaction cell, a water-blank is measured and then absorbance readings are taken 57 times in 10 minutes, thus yielding a total of 57 measure points for the absorbance at each wavelength. The concentration can be calculated by using at least one of these measurement points. The measurements are performed at 37 degrees Celsius.

For the analyte CRP (direct assay format) the first wavelength was determined by 505 nm and second wavelength by 600 nm, while the standard wavelength is 570 nm. The first reaction time was determined by 2.0 min and second reaction time by 1.2 min, while the standard reaction time is 2.0 min. For the first and second calibration curves as well as for the standard calibration curve 800 nm was recorded and used for correction purposes by blanking.

For the analyte Ferritin (direct assay format) the first wavelength was determined by 505 nm and the second wavelength by 570 nm, while the standard wavelength is 570 nm. The first reaction time was determined by 4.9 min and second reaction time by 5.1 min, while the standard reaction time is 5.1 min. For the first and second calibration curves as well as for the standard calibration curve 800 nm was recorded and used for correction purposes by blanking.

For the analyte Myoglobin (direct assay format) the first wavelength was determined by 505 nm and the second wavelength by 660 nm, while the standard wavelength is 570 nm. The first reaction time was determined by 6.7 min and second reaction time by 2.6 min, while the standard reaction time is 4.7 min. For the first and second calibration curves as well as for the standard calibration curve 800 nm was recorded and used for correction purposes by blanking.

For the analyte D-Dimer (direct assay format) the first wavelength was determined by 800 nm and the second wavelength by 700 nm, while the standard wavelength is 800 nm. The first reaction time was determined by 4.3 min and second reaction time by 1.4 min, while the standard reaction time is 4.3 min.

For the analyte Rheuma-factor II (direct assay format) the first wavelength was determined by 546 nm and the second wavelength by 660 nm, while the standard wavelength is 570 nm. The first reaction time was determined by 8.5 min and second reaction time by 1.4 min, while the standard reaction time is 2.2 min. For the first and second calibration curves as well as for the standard calibration curve 800 nm was recorded and used for correction purposes by blanking.

For the analyte DIG (digoxin) (competitive assay format) the first wavelength was determined by 660 nm and the second wavelength by 505 nm, while the standard wavelength is 660 nm. The first reaction time was determined by 4.7 min and second reaction time by 4.7 min., while the standard reaction time is 4.7 min. For the second calibration curve 800 nm was recorded and used for correction purposes by blanking.

For the analyte Phenobarbital (competitive assay format) the first wavelength was determined by 600 nm and the second wavelength by 505 nm, while the standard wavelength is 600 nm. The first reaction time was determined by 6.5 min and second reaction time by 7.9 min, while the standard reaction time is 6.5 min. For the first and second calibration curves as well as for the standard calibration curve 800 nm was recorded and used for correction purposes by blanking.

In most cases the dynamic range was improved by the use of the approach from the present disclosure, either by improving the LDL and/or the UDL of the assay. Only in the case of digoxin and D-Dimer the improvement is moderate.

From these assay examples depicted above some trends can be deduced for the direct assay format. The first wavelength, used for the first calibration curve and for the sensitive detection of the analyte, is usually smaller than the second wavelength, used for the second calibration curve and the detection of high analyte concentrations. An exception is shown for the D-Dimer assay. In addition, the first reaction time is larger or identical to the second reaction time in most cases An exception is identified for the Ferritin assay, showing a first reaction time that is smaller than the second reaction time. Similar trends are observed for the assay with the competitive assay format that seem to behave vice versa to the assays with the direct format.

In accordance with one embodiment of the present disclosure, a further wavelength is optionally determined as a blank value for the correction of interferences and compensation of photometric noise, also known as bichromatic measurement (din. Chem. 1979, 25, 1482-1484). For each of the two main wavelengths it is optional if a further wavelength is recorded for correction purposes by subtraction of the signal at the correction wavelength from the signal at the main wavelength. Typically, for the analyte CRP, this further wavelength for the corrections is recorded at 800 nm.

For the "first wavelength" and first reaction time and for the "second wavelength" and second reaction time, calibration curves are constructed with standard samples for a specific analyte, which are simultaneously measured. According to the present disclosure, the first calibration curve recording at the first wavelength ($\lambda 1$) and first reaction time (t1) is optimized for sensitivity or lower detection limit (LDL). The second calibration curve recording at the second wavelength ($\lambda 2$) and the second reaction time (t2) is optimized for high upper detection limit (UDL). As an example, for the CRP-assay standard samples are simultaneously measured at all 12 wavelengths available on the Roche COBAS C 311 analyzer, including $\lambda 1$ (=505 nm) and $\lambda 2$ (=600 nm) and the correction wavelength (800 nm), over a time period of 10 min (=complete reaction time). By correcting all the absorbance values at 505 nm measured during the complete reaction time (approximately 10 min) via subtraction of the corresponding absorbance values at 800 nm, followed by the calculation of the signal values for the first reaction time (t1) hereof by calculating the difference between the absorbance value at the time shortly after the final reagent is added to the reaction mixture and the absorbance value recorded 2.0 min after the final reagent was added to the reaction mixture, calibration curve 1 is obtained; and simultaneously by correcting all the absorbance values at 600 nm measured during the complete reaction time (approximately 10 min) via subtraction of the corresponding absorbance values at 800 nm followed by the calculation of the signal values for the second reaction time (t2) hereof by calculating the difference between the absorbance value at the time shortly after the final reagent is added to the reaction mixture and the absorbance value recorded 1.2 min after the final reagent was added to the reaction mixture calibration curve 2 is obtained.

In accordance with yet another embodiment of the present disclosure, a method is provided wherein two calibration curves are generated, which are recorded at the same wavelengths and at different reaction times.

After constructing calibration curves 1 and 2 for the specific analyte, the concentration of the samples can be determined. Therefore, a sample containing a specific analyte to be determined is added to the test reagents into a cuvette. This mixture is incubated for a certain reaction time, here the complete reaction time, e.g., 10 min.

The term "optical signal" for this analyte, also called absorbance as used herein, is measured simultaneously in the reaction mixture at least at the two predetermined wavelengths, the first and second wavelengths, in one run over the complete reaction time. Optionally, the optical signal at the correction wavelength may be recorded as well.

The term "threshold value" as used herein, also called "cut-off value", is used for defined absorbance values or a defined amount of the analyte of the present method; absorbance values are typically used. Ideally the threshold value is taken from the point where the two calibration curves of the present method change from the first calibration curve to the second calibration curve. Only one absorbance value may be defined as threshold, either a value ($A[\lambda 1,t1]$) for the first wavelength and first reaction time or a value ($A[\lambda 2,t2]$) for the second wavelength and the second reaction time, or two absorbance values ($A[\lambda 1,t1]$ and $A[\lambda 2,t2]$) may be considered in parallel. As an example, for the CRP assay $A[\lambda 1,t1]$ and/or $A[\lambda 2,t2]$ may be defined as threshold values, which correspond to a concentration of 73 mg/l for CRP. In case of assays with increasing calibration curves as it is the case with CRP, the value $A[\lambda 1, t1]$ is the highest signal value of calibration curve 1, and $A[\lambda 2, t2]$ is the lowest signal value of calibration curve 2. Also the raw absorbance signals corresponding to the absorbance values $A[\lambda 1, t1]$ and/or $A[\lambda 2, t2]$ may be defined as threshold. If at least one optical signal of a sample or at least one signal value calculated hereof exceeds the corresponding predetermined threshold value, the concentration of the analyte is determined by comparison with the second calibration curve of the second wavelength and second reaction time. It is important for an IVD assay that the threshold values are chosen at a concentration that does not coincide with the clinical decision value.

For the selection of the point where the two calibration curves of the present method change from the first calibration curve to the second calibration curve there is usually a broad flexibility. Important is that at the selected point both curves fulfill the requirements related with the linearity of the method and with the precision and with the sensitivity. For example, calibration curve 2 ideally should have an LDL which at least covers the concentration at the selected point; and calibration curve 1 ideally should show linearity of the method at least up to the said selected point.

The selection of the optimal first wavelength and first reaction time for the first calibration curve, characterized by yielding an optimal LDL, as well as the selection of the optimal second wavelength and second reaction time for the second calibration curve, characterized by yielding an optimal UDL, were performed by a trial-and-error procedure. Although there are some trends for choosing the optimal wavelengths and reaction times, there are also exceptions from the trends, and as consequence all combinations of wavelengths and reaction times have to be checked for their capacity to yield an optimal LDL or UDL. However, when doing these calculations manually, i.e., without the aid of automated calculation tools or algorithms, it is not possible to make the LDL- and UDL-calculations for all combinations of wavelengths and reaction times with reasonable efforts and in a reasonable time period. For this reason the following procedure was used in the present disclosure for the development of a method for a certain assay, with other words for the selection of the optimal first wavelength and reaction time as well as for the second wavelength and reaction time as well for the threshold:

1) Measurement of the absorbance values of the following samples simultaneously at the 12 wavelengths available, e.g., on the Roche COBAS C 311 analyzer over the complete reaction time:
   at least 6 standards in duplicates for the calibration,
   a blank sample in 21 replicates for determination of LDL,
   at least 2 samples in 21 replicates for the determination of the precision (coefficient of variation),
   dilution series covering concentrations, e.g., 2-4 fold higher than the known UDL for the determination of the UDL and the linearity of the method.

2) Selection of the first reaction time t1 and first wavelength $\lambda 1$ for the first calibration curve is performed by analyzing the 12 kinetic curves, recorded at the 12 different main wavelengths over the complete reaction time, of the blank sample (21 replicates) and a low concentrated sample. Optionally correction wavelengths may be additionally considered thus increasing the number of kinetic curves to be analyzed for the selection of the best wavelengths and reaction times. The low concentrated sample has a concentration in the range of 1-5-fold of the known LOQ value and may be one of the standard samples or one of the precision samples measured under point 1). The kinetic curves describe the absorbance values in the y axis and the time (in case of the Roche COBAS C 311 analyzer the time is depicted as measure point) in the x axis. Only absorbance values within the specified optical range of the detector (0.0000-3.0000 absorbance) are considered. In the first step some optimal reaction times are determined for each wavelength from the corresponding kinetic curve by choosing an initial time point (or measure point), before or shortly after the final reagent is added, and by choosing a final time point (or measure point), fulfilling the following guidelines:
   the signal variation of the blank sample (21 replicates) is minimal and the signal of the blank sample is low at the initial time point,
   the absorbance reading for the low concentrated sample is low at the initial time point and high at the final time point, i.e., the difference between the initial absorbance reading and final absorbance reading is maximal.

The term "reaction time" as used herein is the difference from the initial time point from the final time point. After having selected some optimal reaction times for each wavelength, the LDL for all 12 wavelengths at these reaction times are calculated. The wavelength and reaction time yielding the best LDL are selected as the first wavelength and first reaction time for the generation of the first calibration curve.

3) Selection of the second reaction time t2 and second wavelength $\lambda 2$ for the second calibration curve is performed by analyzing the 12 kinetic curves, recorded at the 12 different main wavelengths over the complete reaction time, of the dilution series covering concentrations, e.g., 2-4 fold higher than the known UDL. Optionally, correction wavelengths may be additionally considered thus increasing the number of kinetic curves to be analyzed for the selection of the best wavelengths and reaction times. Only absorbance values within the specified optical range of the detector (0.0000-3.0000) are considered. In the first step some optimal reaction times are determined for each wavelength from the corresponding kinetic curve by choosing an initial time point (or measure point), before or shortly after the final reagent is added, and by choosing a final time point (or measure point), fulfilling the following criteria:
   the initial time point is chosen at a point before or shortly after the final reagent is added;
   the final time point is chosen in such way that the highest concentrated samples of the dilution series show distinguishable and increasing signals with increasing concentrations, i.e., the absolute value of the difference between the initial
   absorbance reading and final absorbance reading for a certain concentrated sample is higher than the corresponding absolute value of the difference value for the next lower concentrated sample.

After having selected some optimal reaction times (difference from the initial time point from the final time point) for each wavelength, the UDL for all 12 wavelengths at these reaction times are calculated. The wavelength and reaction time yielding the best UDL are selected as the second wavelength and second reaction time for the generation of the second calibration curve.

4) Threshold setting: The threshold values are set at a concentration where the calibration curves change from the first to the second calibration curve, i.e., for lower concentrations the first calibration curve is used for the analyte quantification and for higher concentrations the second calibration curve is used for the analyte quantification. For the selection of the point or the concentration where the calibration curves change, there usually exist a broad flexibility. At this point it is important that the following criteria are fulfilled:

- that both calibration curves show linearity of the method; the first calibration curve in the range from the LDL to the concentration at the threshold, and the second calibration curve in the range from the concentration at the threshold to the UDL,
- that the second calibration curve shows a LDL that at least covers the concentration at the threshold;
- that the concentration at the threshold is not identical with the clinical decision value of the IVD test.

An additional embodiment of the present disclosure is therefore a computer-implemented method for determining the optimal wavelength, reaction time and threshold according to the present disclosure, comprising the steps of:

a) receiving a dataset representing the absorbance values of the samples simultaneously available on an analyzer, wherein the dataset including a plurality of data points:
  standards in duplicates for the calibration,
  a blank sample for determination of LDL,
  at least 2 samples in replicates for the determination of the precision;
b) dilution series covering concentrations determining of the first reaction time and first wavelength for the first calibration curve by analyzing the kinetic curves, recorded at different main wavelengths over the complete reaction time, of the blank sample and a low concentrated sample;
c) determining of the second reaction time and second wavelength for the second calibration curve by analyzing the kinetic curves, recorded at different main wavelengths over the complete reaction time; and
d) setting the threshold values at a concentration where the calibration curves change from the first to the second calibration curve, by using for lower concentrations the first calibration curve for the analyte quantification and by using for higher concentrations the second calibration curve for the analyte quantification.

In accordance with still yet another embodiment of the present disclosure, is a computer readable medium including code controlling a processor for determining the optimal wavelength, reaction time and threshold is provided, the code including instructions for:

a) receiving a dataset representing the absorbance values of the samples simultaneously available on an analyzer, wherein the dataset includes a plurality of data points:
  standards in duplicates for the calibration,
  a blank sample for determination of LDL,
  at least 2 samples in replicates for the determination of the precision;
b) dilution series covering concentrations determining of the first reaction time and first wavelength for the first calibration curve by analyzing the kinetic curves, recorded at different main wavelengths over the complete reaction time, of the blank sample and a low concentrated sample;
c) determining of the second reaction time and second wavelength for the second calibration curve by analyzing the kinetic curves, recorded at different main wavelengths over the complete reaction time; and
d) setting the threshold values at a concentration where the calibration curves change from the first to the second calibration curve, by using for lower concentrations the first calibration curve for the analyte quantification and by using for higher concentrations the second calibration curve for the analyte quantification.

In an exemplary embodiment of the present disclosure, the method may be implemented by using conventional personal computer systems including, but not limited to, an input device to input a data set, such as a keyboard, mouse, and the like; a display device to represent a specific point of interest in a region of a curve, such as a monitor; a processing device necessary to carry out each step in the method, such as a CPU; a network interface such as a modem, a data storage device to store the data set, a computer code running on the processor and the like. Furthermore, the method may also be implemented in an analyzer, e.g., Roche COBAS C 311 analyzer.

In the case that these criteria are not fulfilled for the threshold at any concentration, either the conditions for the first calibration curve (first wavelength and first reaction time) and/or the conditions for the second calibration curve (second wavelength and second reaction time) have to be changed so that the criteria are fulfilled. Such changes may compromise the achieved improvement factor for the dynamic range. In the procedure described above for the selection of the optimal wavelengths and reaction times for calibration curves 1 and 2 only the two-point-end method was applied for calculating the signals. A two-point-end method is an end-point-assay which performs a sample blank. Here two absorbance readings at two different measure points are considered: the first reading is usually taken before or shortly after the final reagent is added; the second reading is taken at any time point after the final reagent was added. Principally, for the selection of the optimal first wavelength and first reaction time as well as for the second wavelength and second reaction time a kinetic signal calculation method can be additionally considered and which may yield for certain assays better results compared to the two-point-end method.

By selecting either the first or the second calibration curve for the quantification of the specific analyte, which depends on the optical signal of the sample to be determined, an extended dynamic range or measuring range is achieved.

The term "extended dynamic range" as used herein means that samples with a very low concentration of the specific analyte and/or samples with a very high concentration of the specific analyte can be determined, which is not the case in standard methods using only one main wavelength and one calibration curve. According to the present disclosure, the improvement of the lower detection limit and/or of the upper detection limit results in an improved dynamic range.

According to the present disclosure, "a high concentration of a specific analyte" as used herein is not causing a High-dose "Hook-effect". The hook-effect is a common phenomenon in everyday work of a clinical laboratory. Primarily, the hook-effect depends on analyte concentration, it is an excessive amount of analyte that overwhelms the binding capacity of the capture antibody. This results in an inappropriately low signal that causes an erroneous low or normal result ("hooked" result) for a sample with an excessively elevated analyte concentration. It implies the presence of huge excess of analyte, which saturates all binding sites on antibody. A hook-effect is existent, if in diluted samples higher values are measured than in nondiluted sample. Some automated analyzers have a system for recognizing excess of an analyte while the sample is being simultaneously diluting. According to the present disclosure an excessive amount of a specific analyte causing a High-dose "Hook-effect" cannot be prevented by comparison with the second calibration curve.

One embodiment of the present disclosure is the provision of cases for correcting calibration curves. The analyte CRP is measured at 505 nm for the first wavelength for the sensitive detection and at 600 nm for the second wavelength for the upper detection limit. The third wavelength is recorded at 800 nm for correcting interferences and compensations of most of the photometric noise in the first and second calibration curve.

The term "complete reaction time" as used herein is the time period of measuring a specific analyte at a plurality of wavelengths. For the selection of the best two wavelengths aimed at the generation of the two calibration curves standards were simultaneously measured at the 12 different wavelengths available on the Roche COBAS C instrument. Only absorbance values lying within the optical range of the detector (0.0000-3.0000 absorbance) were taken into consideration.

The typical complete reaction time of the present immunoassay time varies between 1 and 20 minutes. Typically, the complete reaction time of a multiple wavelength spectrophotometer is around 10 minutes. It is an embodiment of the present disclosure that the optical signals of the specific analyte are measured during the complete reaction time. Most typically, the optical signal of the specific analyte is measured simultaneously at least at the first and at the second main wavelengths. The term "time delay" as used herein is the time period between the first and at the second main wavelength for the detection of the specific analyte.

The term "simultaneously" as used in accordance with the present disclosure, may imply a time delay smaller than about 60× seconds, e.g., a time delay smaller than about 10× seconds, typically smaller than about 1× second, most typically smaller than 1 ms, or even smaller 0.1×ms. Most typically, the term "simultaneously" means no time delay.

A further aspect of the present disclosure is a method for increasing the sensitivity and/or dynamic range of photometric assays, wherein the specific analyte in a sample reacts with an analyte specific reaction partner in a reaction mixture, comprising the steps of generating at least two calibration curves, wherein the first calibration curve recorded at a first wavelength is optimized for low concentrations of the specific analyte thereby maximizing the lower detection limit, and the second calibration curve recorded at a second wavelength is optimized for high concentrations of the specific analyte thereby maximizing the upper detection limit, the optical signal is measured simultaneously for the specific analyte of a sample to be determined in the reaction mixture, at least at the first and second wavelengths. Either the first or the second calibration curve is selected for quantification of the specific analyte, by the following criteria:

For increasing calibration curves:

If the optical signal of the first and/or the second wavelength is lower than a corresponding predetermined threshold value, the concentration of the analyte is determined by the use of the first calibration curve recorded at the first wavelength. If the optical signal of the first and/or the second wavelength exceeds a corresponding predetermined threshold value, the concentration of the analyte is determined by the use of the second calibration curve recorded at the second wavelength, and finally quantifying the amount of the specific analyte.

For decreasing calibration curves:

If the optical signal of the first and/or the second wavelength is lower than a corresponding predetermined threshold value, the concentration of the analyte is determined by the use of the second calibration curve recorded at the second wavelength. If the optical signal of the first and/or the second wavelength exceeds a corresponding predetermined threshold value, the concentration of the analyte is determined by the use of the first calibration curve recorded at the first wavelength and finally quantifying the amount of the specific analyte. Typically, two calibration curves for a first and a second wavelength and reaction times are generated, which were predetermined for a specific analyte. According to the present disclosure, the lower detection limit and the upper detection limit both results in an increase of the sensitivity and/or dynamic range. The benefit is a reduced number of re-runs leading to a higher throughput of samples and a reduced turn-around-times. Furthermore, reduced test costs and improved reliability.

The present disclosure leads to an improvement shown for the lower detection limit (LDL) and/or upper detection limit (UDL). Typically, a 1 to 2 times improvement is shown for the lower detection limit (LDL) and/or upper detection limit (UDL). More typically, a 3 to 4 times improvement is shown for the lower detection limit (LDL) and/or upper detection limit (UDL). Most typically, the present disclosure leads to a 5 times improvement shown for the lower detection limit (LDL) and/or upper detection limit (UDL). Typically, the improvement factor is higher than factor 1, more typically the factor is higher than factor 3, and most typically the improvement factor is higher than factor 5 as shown for the RF II direct assay.

A further aspect of the present disclosure is a method for determining the amount of CRP by turbidimetric and nephelometric immunoassays, wherein CRP in a sample is quantified from the change in the turbidity of the reaction mixture based on the aggregation of CRP and a CRP binding partner. Two calibration curves are generated for a first and a second wavelength and corresponding first and second reaction time, which were predetermined for CRP. The optical signal for CRP of a sample to be determined is measured simultaneously in the reaction mixture at least at the first and second wavelengths during the complete reaction time. The first wavelength is optimized for low concentrations of CRP thereby maximizing the lower detection limit, the second wavelength is optimized for high concentrations of CRP thereby maximizing the upper detection limit. Either the first or the second wavelengths and the first or second reaction time are selected for quantification of CRP. If at least one of the optical signal of a sample measured during the complete reaction time or at least one signal value calculated hereof is lower than a corresponding predetermined threshold value, the concentration of CRP is determined by comparison with the calibration curve of the first wavelength and first reaction time. On the other hand, if at least one of the optical signal of a sample or at least one signal value calculated hereof exceeds the corresponding predetermined threshold value, the concentration of CRP is determined by comparison with the calibration curve of the second wavelength and second reaction time.

In the case of the CRP test the calibration curve recorded at 505 nm with a reaction time of 2.0 min and corrected at 800 nm yielded the best LDL (0.036 mg/L). The comparison between the standard performance and the approach of the present disclosure results in an increase of the sensitivity (LDL) by a factor of 1.8 and an extension of the dynamic range by a factor of approximately 3.1. The calibration curve 2 recorded at 600 nm with 1.2 min reaction time and corrected at 800 nm resulted the best UDL (660 mg/L). The UDL shows an increase of a factor of 1.8 compared to standard conditions.

Furthermore, for particle-enhanced turbidimetric assays the combination of the approach of the present disclosure with adapted particle sizes and antibody loading degrees was assessed using the CRP L3 assay as lead parameter. The CRP L3 assay includes two different types of particles as described in European Patent No. 08 98169, large latex particles (MP2) coated with highly affine antibodies and small latex particles (MP1) coated with less affine antibodies (clone 21F12, concentration for latex coating: 45 mg/g latex).

An additional improvement of the CRP-assay sensitivity was yielded by using large particles between 230-400 nm, more typically 250-350 nm, most typically 280-320 nm diameter for increased light scattering efficiency and using a high loading degrees of the particles with antibody, obtained by using a concentration of the antibody between 55-70 mg IgG/gram particles, typically 60-70 mg IgG/gram particles for their conjugation to the particles.

The combination of the method of the present disclosure with large particle sizes between 230-330 nm and an antibody concentration between 55-70 mg IgG/gram particles for conjugation reaction leads to a further increase of the sensitivity (LDL) in comparison to the standard assay (size of large particles: 220 nm, antibody concentration of 50 mg IgG/gram particles for the conjugation of the large particles; size of small particles: 110-140 nm) by a factor of approximately eight and therefore to an extension of the dynamic range by a factor of approximately eight.

In accordance with a further embodiment of the present disclosure, a method is provided, wherein for the specific analyte CRP a particle size for large particles between 230-400 nm and for small particles around 110-140 nm and an antibody concentration of 55-70 mg IgG/gram particles for conjugation reaction for the conjugation of the large particles is used.

The first calibration curve was recorded at a first wavelength of 505 nm with 800 nm as correction wavelength and a first reaction time of 2.8 min; the second calibration curve was measured at 570 nm as main wavelength and 800 nm as correction wavelength and a reaction time of 2.0 min. The standard method has only one calibration curve, measured at 570 nm as main wavelength and 800 nm as correction wavelength and a reaction time of 2.0 min.

A further aspect of the present disclosure is the use of at least two wavelengths and at least two reaction times predetermined for a specific analyte for the generation of at least two calibration curves for quantifying the amount of a specific analyte of photometric assays, wherein a first calibration curve recorded at a first wavelength is optimized for low concentrations of the specific analyte thereby maximizing the lower detection limit, and second calibration curve recorded at a second wavelength is optimized for high concentrations of the specific analyte thereby maximizing the upper detection limit and the optical signal of the specific analyte at the first and second wavelengths is measured simultaneously during the complete reaction time.

Another aspect of the present disclosure is a system analyzer comprising a sample container and an assay reagent container, a reaction container for receiving and mixing the sample and the assay reagents, a photometer for measuring the reaction mixture of step b and means for outputting the analysis result for determining the amount of a specific analyte according to the present invention.

FIG. 1 shows the calibration curves at different wavelengths of the CRP-assay. Six standards were simultaneously measured at the 12 different wavelengths available on the COBAS C instrument (Roche Diagnostics GmbH). Only absorbance values lying within the optical range of the detector (0.0000-3.0000 absorbance) were taken into consideration. Here, five calibration curves are shown as examples, which were recorded at 5 different main wavelengths out of the 12 possible wavelengths, for the main wavelengths 480-nm, 505-nm, 546-nm, 570-nm and 600-nm. All curves were corrected at the wavelength 800 nm and taken at a reaction time of 2.0 min.

FIG. 2 shows the improvement obtained with the CRP assay by application of the method of the present disclosure in combination with different particle sizes and different antibody loadings of the particles.

In the first example, the new approach was combined with particle adaptation aimed at the increase of the sensitivity (LDL). The combination of the new approach with larger particle sizes (290 nm instead of 220 nm diameter of MP2 particles) for increased light scattering efficiency and higher antibody loading degrees (antibody concentration of 60 mg IgG/g particles for conjugation reaction of the large particles) for increased immune reactivity leads to an increase of the sensitivity (LDL) by a factor of approximately eight and an extension of the dynamic range by a factor of eight.

In the second example, the sizes and antibody loading of both particles, the large particles MP2 as well as the small particles MP1, were modified:
larger MP2 particles (290 nm instead of 220 nm), conjugated with an antibody concentration of 70 mg IgG/g particles, and
smaller MP1 particles (90 nm instead of 110-140 nm) conjugated with an antibody concentration of 50 mg IgG/g particles.

These new particles yielded an improved LDL by a factor of 3 and an improved UDL of a factor of approximately 2 compared to the standard assay (MP1: 110-140 nm with 45 mg IgG/g, and MP2: 220 nm with 50 mg IgG/g).

Figure 3:
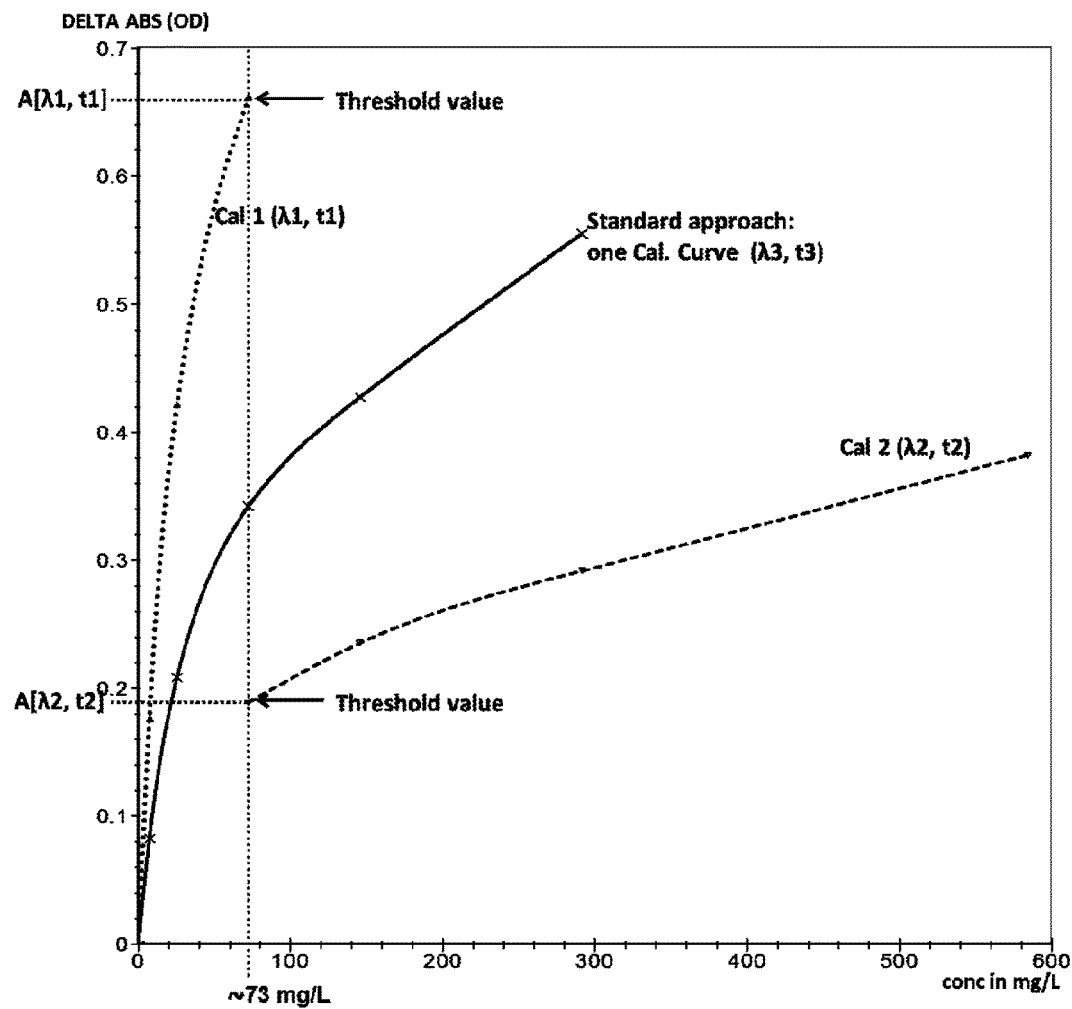
FIG. 3 shows schematically how the threshold values may be placed for the selection of one of the two calibration curves of the present disclosure.

FIG. 3 shows schematically how the threshold values may be placed for the selection of one of the two calibration curves of the present disclosure.

Figure 4:
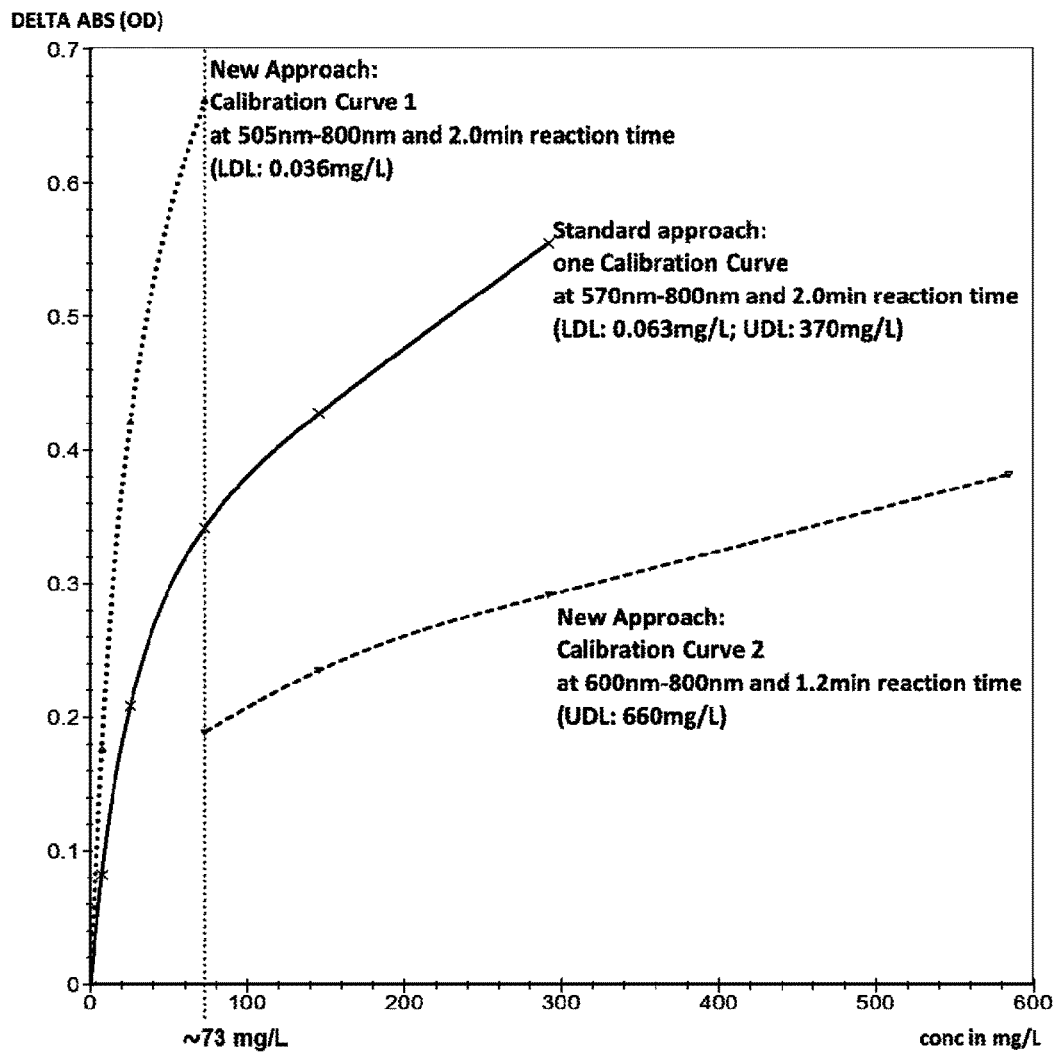
FIG. 4 shows calibration curves for the exemplary CRP-assay in accordance with one embodiment of the present disclosure.

FIG. 4 shows calibration curves for the CRP-assay. The standard calibration curve is obtained by measuring at 570-800 nm. Calibration curve 1 (Cal 1) recorded at 505-800 nm and a reaction time of 2.0 min yielded the best LDL (0.036 mg/L). The calibration curve 2 (Cal 2) recorded at 600-800 nm and 1.2 min reaction time resulted in the best UDL (660 mg/L). The threshold value for CRP may be defined as at least one of the two absorbance values at 73 mg/L.

FIG. 5 shows the benefit of the new approach by using commercial tests available from the product portfolio of Roche Diagnostics GmbH. The analytes that were determined are Ferritin, Myoglobin, D-Dimer, Rheuma factor II (RF II), CRP, Digoxin (DIG), Phenobarbital (PHENO). In the second column the conditions for standard calibration curves are shown. Columns three and four show the new conditions for calibration curves 1 and 2. For each specific analyte the best wavelengths for LDL and UDL and the improvement factors for LDL, UDL were determined. In most cases the new approach improves the dynamic range without any modification of reagents or formulations.

Figure 6A:
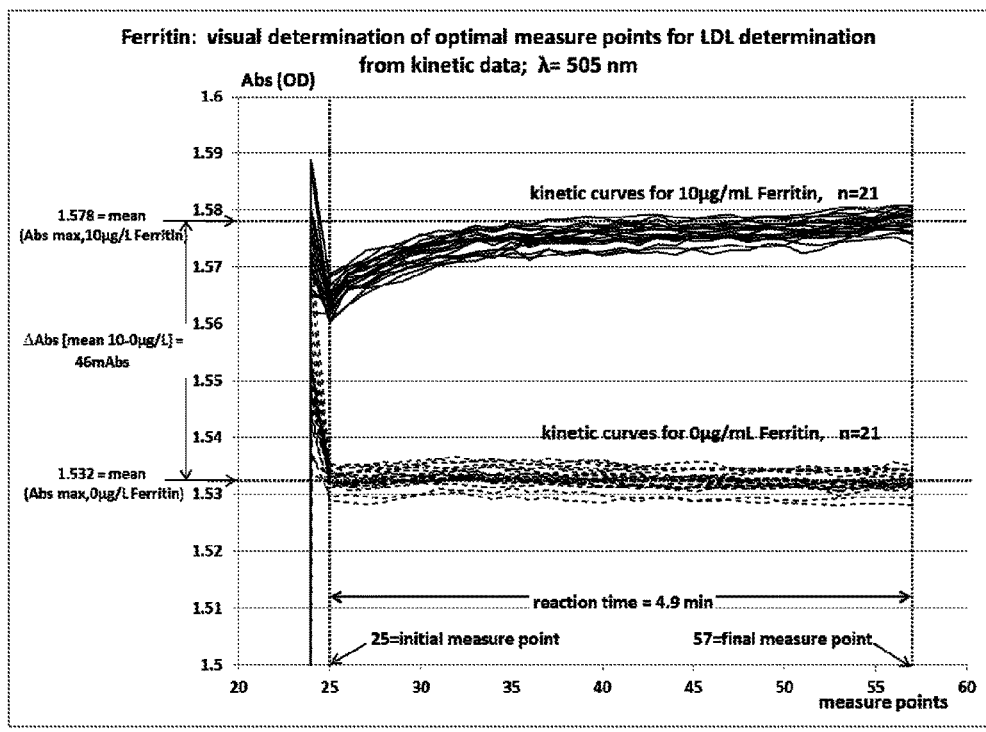
FIGS. 6A and 6B show kinetic curves for an exemplary ferritin assay showing the signal magnitude (absorbance) of a low concentrated sample (10 µg/ml ferritin; 21 replicates) and a blank sample (0 µg/ml ferritin; 21 replicates) at two different main wavelengths, 505 nm and 570 nm, respectively.
Figure 6B:
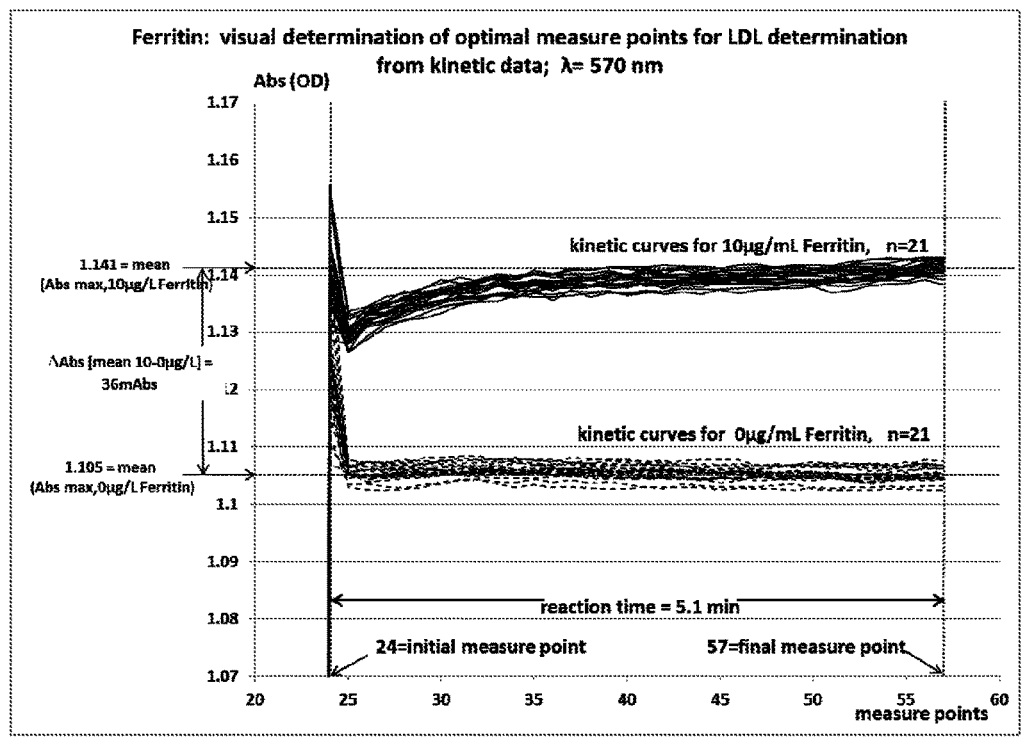

FIGS. 6A and 6B show exemplary kinetic curves for the ferritin assay showing the signal magnitude (absorbance) of a low concentrated sample (10 µg/ml ferritin; 21 replicates) and a blank sample (0 µg/ml ferritin; 21 replicates) at 2 different main wavelengths, 505 nm (FIG. 6A) and 570 nm (FIG. 6B). The kinetic curves describe the absorbance values in the y axis and the time (in case of the Roche COBAS C 311 analyzer the time is depicted as measure point) in the x axis. Optimal reaction times for the first calibration curve are determined by choosing an initial time point (or measure point), before or shortly after the final reagent is added, and by choosing a final time point (or measure point), fulfilling the following guidelines:

the signal variation of the blank sample (21 replicates) is minimal and the signal of the blank sample is low at the initial time point the absorbance reading for the low concentrated sample is low at the initial time point and high at the final time point, i.e., the difference between the initial absorbance reading and final absorbance reading is maximal.

The reaction time is the difference from the initial time point from the final time point. In most cases, the higher the signal magnitude of the low concentrated sample the better LDL values are obtained provided the standard deviation of the blank sample is comparable.

Figure 7:
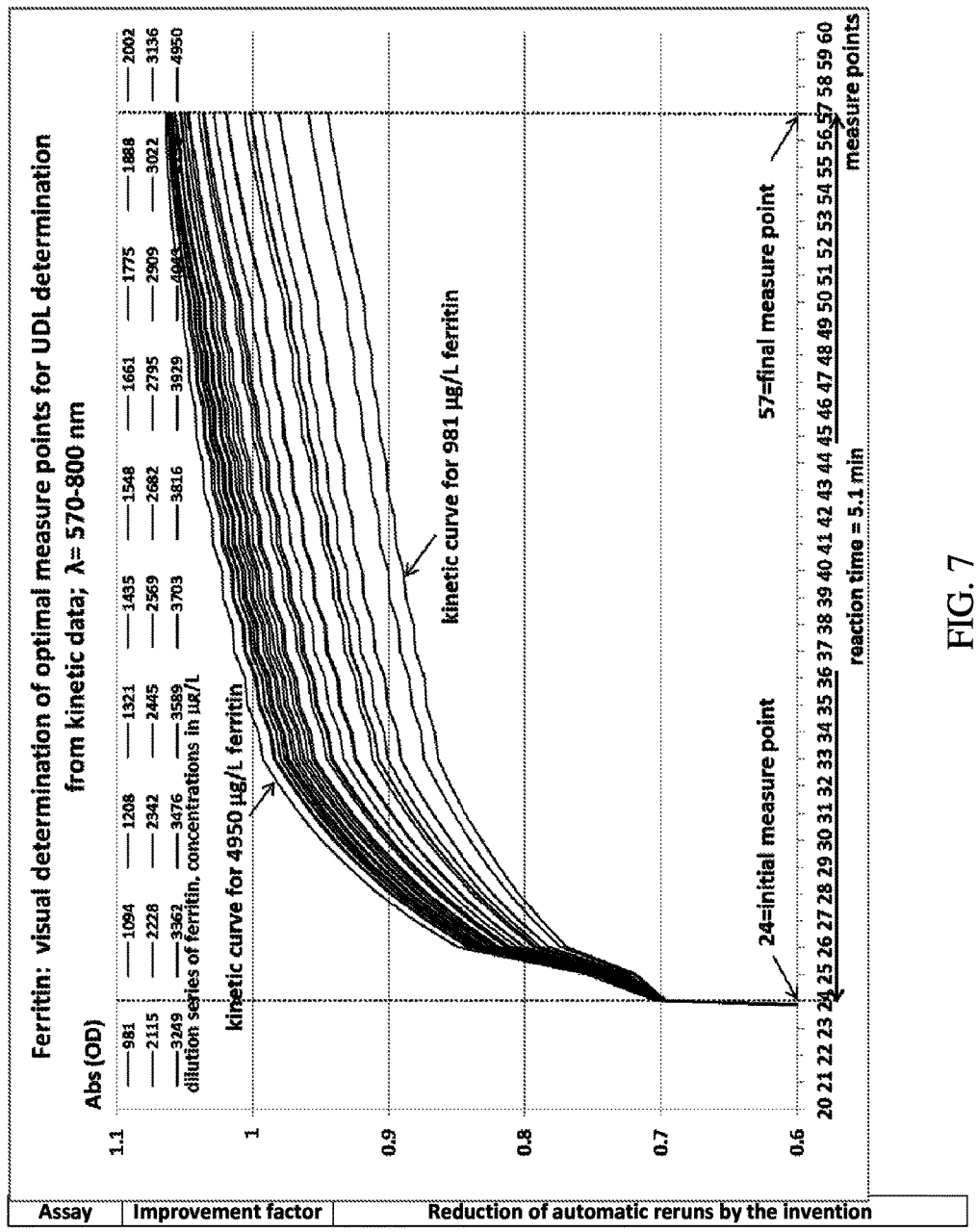
FIG. 7 shows exemplary kinetic curves for the ferritin assay showing the signal magnitude (absorbance) of different highly concentrated samples (981-4950 µg/L ferritin) recorded at the main wavelength 570 nm, corrected by the absorbance at the wavelength 800 nm.

FIG. 7 shows exemplary kinetic curves for the ferritin assay showing the signal magnitude (absorbance) of different highly concentrated samples (981-4950 µg/L ferritin) recorded at the main wavelength 570 nm, corrected by the absorbance at the wavelength 800 nm. The kinetic curves describe the absorbance values in the y axis and the time (in case of the Roche COBAS C 311 analyzer the time is depicted as measure point) in the x axis. Optimal reaction times for the second calibration curve are determined by choosing an initial time point (or measure point), before or shortly after the final reagent is added, and by choosing a final time point (or measure point), fulfilling the following criteria:

the initial time point is chosen at a point before or shortly after the final reagent is added;

the final time point is chosen in such way that the highest concentrated samples of the dilution series show distinguishable and increasing signals with increasing concentrations, i.e.; the difference between the initial absorbance reading and final absorbance reading for a certain concentrated sample is higher than the corresponding difference value for the next lower concentrated sample.

The reaction time is the difference from the initial time point from the final time point. Usually, good UDL values are obtained when the signals of the highly concentrated samples are distinguishable and when the signals increase with the sample concentration.

FIG. 8: as shown in table 4 and the examples 6, 7, 8, 9 the application of the present disclosure leads to an extension of the measuring range of commercially available assays.

One benefit of this measuring range extension is that for assays running on automated lab analyzers the re-run rate, which is caused by samples with analyte concentrations exceeding the measuring range, can be reduced. In order to make a rough estimation of the scale of the achievable re-run rate reduction the results obtained for at least 1000 clinical samples per assay on a Roche COBAS C 501 analyzer were analyzed with the standard method and the method of the present disclosure. Samples with analyte concentrations falling out of the measuring range cause an automatic re-run on the analyzer. The achievable measuring range with the standard method is depicted in the package insert document of the applicable commercial test, the disclosure of which is hereby incorporated herein.

ALTL example: by using the method of the present disclosure the measuring range of the assay was extended by a factor of 12.1 compared to the standard method. This dynamic range improvement leads to a reduction of the re-runs in comparison to the standard method: 87% of all re-runs caused by samples with analyte concentrations below the standard measuring range can be avoided by applying the method of the present disclosure; and 99% of all re-runs caused by samples exceeding the standard measuring range can be avoided. The samples used for this study are samples from donors with a health profile comparable with that of patients that occur in standard central labs.

In order that the embodiments of the present disclosure may be more readily understood, reference is made to the following examples, which are intended to illustrate the invention, but not limit the scope thereof.

EXAMPLES

Example 1: Determination of the Dynamic Range of the CRP L3 Test 1.1 Instrument:

The Roche COBAS C 311 analyzer (Roche Diagnostics GmbH), which has a multiple wavelength spectrophotometer as detection unit, was used for the experiments. The instrument automatically pipettes the sample and the assay reagents into reaction cells. Up to 3 different reagents, R1, R2 and R3, may be added to the sample. The instrument uses a tungsten halogen lamp as irradiation source (12 V/50 W) and measures the absorbance simultaneously at 12 different wavelengths (at 340, 376, 415, 450, 480, 505, 546, 570, 600, 660, 700 and 800±2 nm) with a photodiode array consisting of 12 photodiodes. The optical path length is 5.6 mm and the optical range of the detector is 0.0000-3.0000 absorbance. For each reaction cell, a water-blank is measured and then absorbance readings are taken 57 times in 10 minutes, here also called the complete reaction time, thus yielding a total of 57 measure points for the absorbance at each wavelength, also called photometric points or assay points. The concentration can be calculated by using at least one of these measurement points. There are two fundamental types of photometric assays on this instrument: endpoint assays and rate assays. The measurements are performed at 37° Celsius.

1.2 Procedure for the CRP-Assay Using the Standard Approach:

The CRP L3 test (CRPL3, Cat. No. 04956842, available from Roche Diagnostics GmbH), a particle-enhanced immunoturbidimetric assay, was selected for this study. Human CRP agglutinates with latex particles are coated with monoclonal anti-CRP antibodies; the aggregates are determined turbidimetrically. Reagents for all Roche tests are provided in COBAS C packs. These cassettes contain from one to three specially designed reagent bottles and have barcode labels with detailed reagent and test-related information. For CRP L3 tests two reagents are used in the cassette: R1 (TRIS buffer with bovine serum albumin and preservatives), and R2 (Latex particles coated with anti-CRP (mouse) in glycine buffer, immunoglobulins (mouse) and preservative). The procedure described in the package insert from the CRP L3 test was used as standard method.

1.3 Pipetting Scheme:

2 µL sample and 150 µL assay buffer (R1) were added subsequently to the reaction cell, followed by the addition of the latex reagent (R2), diluted with 24 µl diluent (water), and mixing of the reaction mixture.

1.4 Conditions for the Generation of the Calibration Curve:

For the measurements 570 nm was used as main wavelength and 800 nm as correction wavelength. The assay type was a two-point-end assay. A two-point-end assay is an end-point-assay which performs a sample blank. Here two absorbance readings at two different measure points are considered: the first reading is usually taken before or shortly after the final reagent is added; the second reading is taken at any time point after the final reagent was added. The absorbance value for the calibration curve and therefore for the concentration calculation is obtained by subtraction of the first reading from the second reading. For CRP L3 the first reading is at measure point 8 and means shortly after the final reagent addition, and the second reading at measure point 18, which corresponds to a reaction time of 2.0 minutes. For the generation of the calibration curve 6 standards from Roche (Cat. No. 11355279) are measured as duplicates with spline as calibration type, which fits the ranges between the data points of the measured calibrators approximated by third degree polynomials so that a smooth calibration curve is obtained.

1.5 Procedure for the CRP-Assay According to the Disclosure:

The reagents used for these experiments were identical to those used for the standard method: see Example 1.2. The procedure described in the package insert from the CRP L3 test was used with exception of the wavelengths and reaction times.

1.6 Pipetting Scheme:

Identical to pipetting scheme 1.3.

1.7 Conditions for the Generation of the Calibration Curve:

The best conditions for both calibration curves were determined as described earlier and the following result was obtained: 505 nm was used as first wavelength, 800 nm as correction wavelength and 2.0 minutes as first reaction time; 600 nm was used as second wavelength, 800 nm as correction wavelength and 1.2 minutes as second reaction time. The assay type was a two-point-end assay as described under Example 1.4.

For the first calibration curve the first reading is at measure point 8 and means shortly after the final reagent addition, and the second reading at measure point 18, which corresponds to a reaction time of 2.0 minutes; for the second calibration curve the first reading is at measure point 8 and means shortly after the final reagent addition, and the second reading at measure point 14, which corresponds to a reaction time of 1.2 minutes. For the generation of both calibration curves each 6 standards covering the corresponding concentrations ranges are measured as duplicates with spline as calibration type, which fits the ranges between the data points of the measured calibrators approximated by third degree polynomials so that a smooth calibration curve is obtained. Similar results were obtained when for both calibration curves the 6 standards from the standard method (Cat. No. 11355279) were used.

The first calibration curve is used which is optimized for a low concentration of the specific analyte thereby maximizing the lower detection limit, the second calibration curve is used which is optimized for a high concentration of the specific analyte thereby maximizing the upper detection limit. Either the first calibration curve or the second calibration curve is to be selected for quantification of CRP, depending on the analyte content or corresponding absorbance of the sample to be quantified. For this purpose the signal of the sample is compared with a predetermined threshold value. The threshold value for CRP may be defined as one of the two or both absorbance values in the calibration curves for CRP, which correspond to a concentration of 73 mg/L (see FIG. 3 or figure new), in other words the absorbance at 505 nm-800 nm for the reaction time of 2.0 minutes (A[$\lambda 1, t1$]=A[505 nm-800 nm, 2.0 minutes]) and/or the absorbance at 600 nm-800 nm for the reaction time of 1.2 minutes (A[$\lambda 2, t2$]=A[600 nm-800 nm, 1.2 minutes]).

If the optical signal of the sample calculated for 505 nm-800 nm and 2.0 minutes reaction time is below the predetermined threshold value A[505 nm-800 nm, 2.0 minutes] and/or if the optical signal of the sample calculated for 600 nm-800 nm and 1.2 minutes reaction time is below the predetermined threshold value A[600 nm-800 nm, 1.2 minutes], the first calibration curve is used for its quantitation.

If the optical signal of the sample calculated for 505 nm-800 nm and 2.0 minutes reaction time exceeds the predetermined threshold value A[505 nm-800 nm, 2.0 minutes] and/or if the optical signal of the sample calculated for 600 nm-800 nm and 1.2 minutes reaction time exceeds the predetermined threshold value A[600 nm-800 nm, 1.2 minutes], the second calibration curve is used for its quantitation. As result two calibration curves are obtained for covering the measuring range for CRP determination, the first covering analyte concentrations from 0 to 73 mg/L and the second covering the range from 73 mg/L to the UDL. Results for the CRP-Assay Using the Standard and the Approach According to an Embodiment of the Disclosure:

1.8 Determination of LDL:

21 replicates of a blank sample were generated and the corresponding signal values x1, x2, . . . x21 calculated, by correcting the absorbance values recorded at the main wavelength of 570 nm by subtraction of the absorbance at 800 nm followed by the subtraction of the value taken at measure point 8 from the value taken at measure point 18. Finally, the mean value x of the 21 signal values x1, x2, . . . x21 and the corresponding standard deviation is calculated. The LDL is determined as the concentration corresponding to the signal value (x+3 SD). For the new approach only the data generated under the first wavelength and first reaction time as well as the corresponding first calibration curve are used.

1.9 Determination of the UDL:

Sample dilution series, covering concentrations approx. 2 to 4 fold higher than the UDL known from the Roche assay, were measured followed by the calculation of the analyte recovery by forming the ratio of measured value to theoretical value. For values between 90% and 110% the method was considered to be linear. The UDL was selected as the highest concentration value within the linear range. For the new approach only the data generated under the second wavelength and second reaction time as well as the corresponding second calibration curve are used.

1.10 Determination of the Coefficient of Variation (CV):

21 replicates of serum samples of certain concentration were measured and the CV of the found concentration values calculated by the ratio of the standard deviation to the mean. For the new approach, depending on the analyte concentration to be assessed, either:

the data generated under the first wavelength and first reaction time as well as the corresponding first calibration curve; or the data generated under the second wavelength and second reaction time as well as the corresponding second calibration curve are used. Two low concentrated samples (1 and 5 mg/L CRP) were assessed for the assay.

1.11 Result Overview and Conclusions:

The result overview is depicted in Table 1. The application of the new approach of CRP test shows an increase of the sensitivity (LDL, lower detection limit) by a factor of 1.8 and an extension of the upper detection limit UDL by a factor of 1.8. The improvement of the corresponding dynamic range is by a factor of 3.1. The precision (CV) obtained with the new method is comparable with the standard method. The new approach affords minimal implementation; the application of the approach does not need any changes of reagents and their formulations. Only the number and concentration of standards for the calibration may be adapted.

TABLE 1

Result overview for CRP L3

| | Standard method (570 nm wavelength, 800 nm correction wavelength, 2.0 min. reaction time) | New method (calibration curve 1: 505 nm wavelength, 800 nm correction wavelength, 2.0 min. reaction time; calibration curve 2: 600 nm wavelength, 800 nm correction wavelength, 1.2 min reaction time) |
|---|---|---|
| LDL (mg/L) | 0.063 | 0.036 |
| UDL (mg/L) | 370 | 660 |
| Dynamic range | 5870 | 18330 |
| Measuring range (mg/L) | 0.063-370 | 0.036-660 |
| CV at 1 mg/L (%) | 5.3 | 5.0 |
| CV at 5 mg/L (%) | 1.8 | 1.7 |

Example 2: Determination of the Dynamic Range of Further Assays 2.1 Instrument:

See Example 1.

2.2 Procedure for the Ferritin Assay Using the Standard Approach:

Roche's ferritin test (FERR4, Cat. No. 04885317), a particle-enhanced immunoturbidimetric assay, was selected for this study. Human ferritin agglutinates with latex particles coated with anti-ferritin antibodies; the aggregates are determined turbidimetrically. Reagents for all Roche tests are provided in COBAS C packs. These cassettes contain from one to three specially designed reagent bottles and have barcode labels with detailed reagent and test-related information. For Ferritin tests two reagents are used in the cassette: R1 (TRIS buffer pH 7.5, immunoglobulins (rabbit) and preservative) and R3 (latex particles coated with anti-human ferritin antibodies (rabbit), preservative). The procedure described in the package insert from the Ferritin test was used as standard method.

2.3 Pipetting Scheme:

10 μL sample and 80 μL assay buffer (R1) were added subsequently to the reaction cell, followed by the addition of the latex reagent (R3) and mixing of the reaction mixture.

2.4 Conditions for the Generation of the Calibration Curve:

For the measurements, 570 nm was used as main wavelength and 800 nm as correction wavelength. The assay type was a two-point-end assay as described under Example 1.4. For ferritin the first reading is at measure point 24 and means shortly after the final reagent addition, and the second reading at measure point 57, which corresponds to a reaction time of 5.1 minutes. For the generation of the calibration curve 6 standards from Roche (Cat. No. 11355279) are measured as duplicates with spline as calibration type, which fits the ranges between the data points of the measured calibrators approximated by third degree polynomials so that a smooth calibration curve is obtained.

2.5 Procedure for the Ferritin Assay According to the Invention:

The reagents used for these experiments were identical to those used for the standard method as described in Example 2.2. The procedure described in the package insert from the ferritin test was used with exception of the wavelengths and reaction times.

2.6 Pipetting Scheme:

Identical to pipetting scheme as described in 2.3.

2.7 Conditions for the Generation of the Calibration Curve:

The best conditions for both calibration curves were determined as described earlier and the following result was obtained: 505 nm was used as first wavelength, 800 nm as correction wavelength and 4.9 minutes as first reaction time; 570 nm was used as second wavelength, 800 nm as correction wavelength and 5.1 minutes as second reaction time. The assay type was a two-point-end assay as described under Example 1.4. For the first calibration curve the first reading is at measure point 25 and means shortly after the final reagent addition, and the second reading at measure point 57, which corresponds to a reaction time of 4.9 minutes; for the second calibration curve the first reading is at measure point 24 and means shortly after the final reagent addition, and the second reading at measure point 57, which corresponds to a reaction time of 5.1 minutes. For the generation of both calibration curves each 6 standards covering the corresponding concentrations ranges are measured as duplicates with spline as calibration type, which fits the ranges between the data points of the measured calibrators approximated by third degree polynomials so that a smooth calibration curve is obtained. Similar results were obtained when for both calibration curves the 6 standards from the standard method (Cat. No. 11355279) were used. The threshold may be defined as one of the two or both absorbance values in the calibration curves for ferritin at a concentration of 100 μg/L.

Results for the Ferritin Assay Using the Standard and the Approach According to the Invention:

2.8 Determination of LDL/UDL/CV:

See Example 1.

2.9 Result Overview and Conclusions:

The result overview is depicted in Table 2. The application of the new approach to Roche's ferritin test shows an increase of the sensitivity (LDL, lower detection limit) by a factor of 1.7 and a retained upper detection limit UDL. The improvement of the corresponding dynamic range is by a factor of 1.7. The precision (CV) obtained with the new method is comparable with the standard method. The new approach affords minimal implementation; the application of the approach does not need any changes of reagents and their formulations. Only the number and concentration of standards for the calibration may be adapted.

TABLE 2

Result overview for FERR4

|  | Standard method (570 nm wavelength, 800 nm correction wavelength, 5.1 min. reaction time) | New method (calibration curve 1: 505 nm wavelength, 800 nm correction wavelength, 4.9 min. reaction time; calibration curve 2: 570 nm wavelength, 800 nm correction wavelength, 5.1 min reaction time) |
|---|---|---|
| LDL (µg/L) | 2.0 | 1.2 |
| UDL (µg/L) | 1940 | 1940 |
| Dynamic range | 970 | 1617 |
| Measuring range (µg/L) | 2-1940 | 1.2-1940 |
| CV at 10 µg/L (%) | 8.9 | 6.7 |
| CV at 30 µg/L (%) | 2.9 | 1.7 |
| CV at 145 µg/L | 0.7 | 0.7 |

Example 3: Assessment of the Dynamic Range Extension Potential of Further Tests from Roche 3.1 Instrument:
See Example 1.
3.2 Procedure for the Assays Using the Standard Approach:

The following particle-enhanced immunoturbidimetric assays from Roche were assessed: three assays with the direct test format, myoglobin (MYO2, Cat. No. 04580010), D dimer (D-DI2, No. 04912551) and rheumatoid factors (RF-II, Cat. No. 20764574), as well as two assays with a competitive test format (KIMS: kinetic interaction of microparticles in solution), digoxin (DIG, Cat. No. 20737836) and phenobarbital (PHNO2, Cat. No. 04490924).

In the DIG assay the particles are coated with digoxin and rapidly aggregate in the presence of antibody solution depending on the digoxin concentration of the sample. In the PHNO2 assay the phenobarbital antibody is covalently coupled to microparticles and the phenobarbital derivative is linked to a macromolecule; the binding of the phenobarbital derivative to the antibody on the microparticles is inhibited by the presence of phenobarbital in the sample. The procedure described in the corresponding package inserts from the above mentioned tests was used as standard method.

3.3 Overview on Reagents, Pipetting and Calibration Procedure:

The procedure was as described in the package insert document from the tests and summarized in Table 3 below.

TABLE 3

Test overview

|  | Reagents | Pipetting scheme | Wavelength, reaction time** | Calibration |
|---|---|---|---|---|
| Myoglobin | R1: Glycine buffer, preservatives. R2: Latex particles coated with anti-myoglobin antibodies, buffer with preservatives. | 3 µL sample, 90 µL R1, 30 µL R2 | 570-800 nm, 4.7 min (7-29) | Standards: 6 point calibration, Cat. No. 04580044. Calibration type: RCM*. Assay type: Two-point-end. |
| D Dimer | R1: Tris buffer, preservatives. R3: Latex particles coated with anti D Dimer antibodies, buffer with preservatives. | 5 µL sample, 90 µL R1, 90 µL R3 | 800 nm, 4.3 min (27-57) | Standards: 6 point calibration, Cat. No. 05050901. Calibration type: Spline. Assay type: Two-point-end. |
| RF II | R1: Glycine buffer, preservatives. R2: Latex particles coated with human IgG, buffer with preservatives. | 3 µL sample, 90 µL R1, 30 µL R2 | 570-800 nm, 2.2 min (7-18) | Standards: 6 point calibration, Cat. No. 12172828. Calibration type: RCM*. Assay type: Two-point-end. |
| DIG | R1: Anti-digoxin antibody in buffer with preservatives. R2: Conjugated digoxin derivative microparticles, buffer with preservatives. | 5.5 µL sample, 84 µL R1, 22 µl R2 (diluted with 20 µl water) | 660 nm, 4.7 min (9-31) | Standards: 6 point calibration, Cat. No. 03375790. Calibration type: RCM*. Assay type: Two-point-end. |
| PHENO | R1: Phenobarbital conjugate in buffer with preservatives. R2: Latex particles coated with anti-phenobarbital | 2 µL sample, 93 µL R1, 93 µL R2 | 600-800 nm, 6.5 min (10-49) | Standards: 6 point calibration, Cat. No. 03375790. Calibration type: RCM*. Assay type: |

TABLE 3-continued

Test overview

| Reagents | Pipetting scheme | Wavelength, reaction time** | Calibration |
|---|---|---|---|
| antibody, buffer with preservatives. | | | Two-point-end. |

*RCM: Rodbard fitting
**main wavelength - correction wavelength; reaction time in minutes; in brackets measure point for first and second reading 3.4 Procedure for the Assays According to the Present Invention:

The reagents used for these experiments were identical to those used for the standard method as described in Example 3.2. The procedure described in the package insert from the ferritin test was used with exception of the wavelengths and reaction times.

the improvement was moderate the improvement factor was set into brackets. The precision (CV) obtained with the new method is comparable with the standard method. The new approach affords minimal implementation; the application of the approach does not need any changes of reagents and their formulations. Only the number and concentration of standards for the calibration may be adapted.

TABLE 4

Result overview

| Roche test | Standard conditions $^d$ | New conditions $^d$ | | Improvement factor $^c$ | | dyn. range |
|---|---|---|---|---|---|---|
| | | Cal 1 | Cal 2 | LDL | UDL | |
| Myoglobin Gen. 2 | 570 nm-800 nm 4.7 min (7-29) | 505 nm-800 nm 6.7 min (9-50) | 660 nm-800 nm 2.6 min (7-20) | 2 $^a$ | 2 | 4 |
| D-Dimer Gen. 2 | 800 nm 4.3 min (27-57) | 800 nm 4.3 min (27-57) | 700 nm 1.4 min (26-33) | — | (1.14) | (1.14) |
| RF II | 570 nm-800 nm 2.2 min (7-18) | 546 nm-800 nm 8.5 min (7-57) | 660 nm-800 nm 1.4 min (7-14) | 5 $^b$ | (1.15) | 5.8 |
| DIG | 660 nm 4.7 min (9-31) | 660 nm 4.7 min (9-31) | 505 nm-800 nm 4.7 min (9-31) | — | (1.15) | (1.15) |
| PHENO | 600 nm-800 nm 6.5 min (10-49) | 600 nm-800 nm 6.5 min (10-49) | 505 nm-800 nm 7.9 min (10-57) | — | 1.5 | 1.5 |

$^a$ Without instrument factor
$^b$ Change calibration to spline
$^c$ Good precision from standard conditions is retained in new conditions
$^d$ First row: main wavelength - correction wavelength; second row: reaction time in minutes, in brackets: measure points 3.5 Overview on Reagents, Pipetting and Calibration Procedure:

The procedure was as described in the package insert document from the tests and summarized in the Table 3, if not mentioned otherwise.

Results for the Assays Myoglobin, D Dimer, RF II, DIG and PHENO Using the Standard and New Approach According to Embodiments of the Disclosure:

3.6 Determination of LDL/UDL/CV:

See Example 1.

3.7 Result Overview and Conclusions:

The result overview is depicted in Table 4. Optimal wavelengths and reaction times for the first and second calibration curves were determined as described earlier. The application of the new approach to the commercial Roche tests leads in most cases to an improvement of the sensitivity (LDL, lower detection limit) and/or to an improvement of the upper measuring range. The improvement of the dynamic range is by a factor of 1.5 to 5.8. In two cases, D dimer and Dig, the improvement is moderate. In cases where Example 4: Additional Improvement of the Dynamic Range for the Combination Assay of the Disclosure with Modified Particles MP2

4.1

In addition, the combination of the assay of the present disclosure with adapted particle sizes and antibody loading degrees was assessed using the CRP L3 assay as lead parameter. The CRP L3 assay includes two different types of particles as described in European Patent No. 0 898 169, large latex particles (MP2, approx. 220 nm diameter) coated with highly affine antibodies (clone 36F12; concentration for latex coating: 50 mg/g latex) and small latex particles (MP1, approx. 110-140 nm diameter) coated with less affine antibodies (clone 21F12, concentration for latex coating: 45 mg/g latex). Here, the MP2 particles were modified by using larger sizes and antibody loading degrees in order to increase the analytical sensitivity, and finally the achievable LDL and dynamic range determined in the assay as described below.

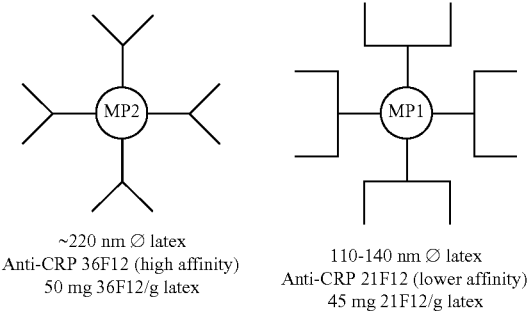

~220 nm ⌀ latex
Anti-CRP 36F12 (high affinity)
50 mg 36F12/g latex 110-140 nm ⌀ latex
Anti-CRP 21F12 (lower affinity)
45 mg 21F12/g latex 4.2 Synthesis of the Modified MP2 Particles:

To latex particles (carboxylate-modified microparticles, 290 nm sized) with a concentration of 2% solids in 750 µl MES buffer (20 mM, pH 6.1) 30 µl of a sulfo-NHS (sulfo-N-hydroxysulfosuccinimide, 100 mM in MES buffer) solution and 30 µl of an EDC (1-Ethyl-3-(3-dimethyllaminopropyl)carbodiimide, 100 mM in MES buffer) solution were successively added. The reaction mixture was shortly sonicated and allowed to react for 1 hour at room temperature on a mixing wheel. Afterwards 60 mg antibody 36F12 per gram latex in 750 µl MES buffer (20 mM, pH 6.1) containing 37 µl of Synperonic P85 solution (1% in MES) were mixed with the sulfo-NHS/EDC-activated latex particles. The reaction mixture was shortly sonicated and allowed to react for 2 hours at room temperature on a mixing wheel. To the reaction mixture 45 µl glycine solution (2M, pH 11) were added, sonicated and mixed for 15 minutes on a mixing wheel. Finally the particles were washed 2 times by centrifugation and resuspension in glycine (50 mM, pH 8) containing 0.03% Synperonic P85. After a final centrifugation and resuspension step the latex particles (1% solids) were stored in glycine (50 mM, pH 8) containing 0.03% Synperonic P85, 0.1% BSA and 0.05% sodium azide.

4.3 Synthesis of the Standard MP1 Particles:

To latex particles (carboxylate-modified microparticles, size 110-140 nm) with a concentration of 2% solids in 750 µl MES buffer (20 mM, pH 6.1) 30 µl of a sulfo-NHS (sulfo-N-hydroxysulfosuccinimide, 100 mM in MES buffer) solution and 30 µl of an EDC (1-Ethyl-3-(3-dimethyllamino-propyl)carbodiimide, 100 mM in MES buffer) solution were successively added. The reaction mixture was shortly sonicated and allowed to react for 1 hour at room temperature on a mixing wheel. Afterwards 45 mg antibody 21F12 per gram latex in 750 µl MES buffer (20 mM, pH 6.1) were mixed with the sulfo-NHS/EDC-activated latex particles. After 20 minutes 37 µl of Synperonic P85 solution (1% in MES) was added to the mixture. The reaction mixture was shortly sonicated and allowed to react for 100 minutes at room temperature on a mixing wheel. To the reaction mixture 45 µl glycine solution (2M, pH 11) were added, sonicated and mixed for 15 minutes on a mixing wheel. Finally the particles were washed 2 times by centrifugation and resuspension in glycine (50 mM, pH 8) containing 0.03% Synperonic P85. After a final centrifugation and resuspension step the latex particles (1% solids) were stored in glycine (50 mM, pH 8) containing 0.03% Synperonic P85, 0.1% BSA and 0.05% sodium azide.

4.4 Preparation of the Reagents R1 and R2 for the Analyser Assay:

The reagents R1 and R2 are as described in the package insert document from the tests. The R2 reagent is prepared by mixing the MP1 and MP2 particles synthesized in steps a) and b). The reagent is filled in a COBAS C pack.

4.5 Instrument:

See Example 1.

4.6 Procedure for the CRP-Assay Using the Standard Approach

Identical to the procedure of Example 1.2.

4.7 Pipetting Scheme:

Identical to pipetting scheme of Example 1.3.

4.8 Conditions for the Generation of the Calibration Curve:

Identical to Example 1.4.

4.9 Procedure for the CRP-Assay Using the Approach of the Present Disclosure:

The reagents used for these experiments were prepared as described above in Example 1.2. The procedure described in the package insert from the CRP L3 test was used with exception of the wavelengths and reaction times.

4.10 Pipetting Scheme:

Identical to the pipetting scheme of Example 1.3.

4.11 Conditions for the Generation of the Calibration Curve:

The best conditions for both calibration curves were determined as described earlier and the following result was obtained: 505 nm was used as first wavelength, 800 nm as correction wavelength and 2.8 minutes as first reaction time; 570 nm was used as second wavelength, 800 nm as correction wavelength and 2.0 minutes as second reaction time. The assay type was a two-point-end assay as described under Example 1.4. For the first calibration curve the first reading is at measure point 8 and means shortly after the final reagent addition, and the second reading at measure point 22, which corresponds to a reaction time of 2.8 minutes; for the second calibration curve the first reading is at measure point 8 and means shortly after the final reagent addition, and the second reading at measure point 18, which corresponds to a reaction time of 2.0 minutes. For the generation of both calibration curves each 6 standards covering the corresponding concentrations ranges are measured as duplicates with spline as calibration type, which fits the ranges between the data points of the measured calibrators approximated by third degree polynomials so that a smooth calibration curve is obtained. Similar results were obtained when for both calibration curves the 6 standards from the standard method (Cat. No. 11355279) were used. The first calibration curve is used which is optimized for a low concentration of the specific analyte thereby maximizing the lower detection limit, the second calibration curve is used which is optimized for a high concentration of the specific analyte thereby maximizing the upper detection limit. Either the first calibration curve or the second calibration curve is to be selected for quantification of CRP, depending on the analyte content or corresponding absorbance of the sample to be quantified. For this purpose the signal of the sample is compared with a predetermined threshold value. The threshold value for CRP may be defined as one of the two or both absorbance values in the calibration curves for CRP which correspond to a concentration of 10 mg/L, with other words the absorbance at 505 nm-800 nm for the reaction time of 2.8 minutes ($A[\lambda 1, t1]=A[505$ nm-800 nm, 2.8 minutes]) and/or the absorbance at 570 nm-800 nm for the reaction time of 2.0 minutes ($A[\lambda 2, t2]= A[570$ nm-800 nm, 2.0 minutes]).

If the optical signal of the sample calculated for 505 nm-800 nm and 2.8 minutes reaction time is below the predetermined threshold value A[505 nm-800 nm, 2.8 minutes] and/or if the optical signal of the sample calculated for 570 nm-800 nm and 2.0 minutes reaction time is below the predetermined threshold value A[570 nm-800 nm, 2.0 minutes, the first calibration curve is used for its quantitation.

If the optical signal of the sample calculated for 505 nm-800 nm and 2.8 minutes reaction time exceeds the predetermined threshold value A[505 nm-800 nm, 2.8 minutes] and/or if the optical signal of the sample calculated for 570 nm-800 nm and 2.0 minutes reaction time exceeds the predetermined threshold value A[570 nm-800 nm, 2.0 minutes], the second calibration curve is used for its quantitation. As result two calibration curves are obtained for covering the measuring range for CRP determination, the first covering analyte concentrations from 0 to 10 mg/L and the second covering the range from 10 mg/L to the UDL. Results for the CRP-Assay Using the Standard and the Approach According to the Present Disclosure:

4.12 Determination of LDL, UDL and CV:

See Example 1.

4.13 Result Overview and Conclusions:

As depicted in FIG. 2 and Table 5, the use of larger MP2 particles (290 nm instead of 220 nm) with higher antibody loading degrees (60 mg 36F12/g latex instead of 50 mg/g) in combination with the multi-application approach leads to an improvement of the LDL and dynamic range by a factor of 8 compared with the commercial standard CRP L3 assay using the standard conditions (latex reagent with unmodified MP1 and MP2 particles; measurement at one main wavelength at 570 nm, corrected by 800 nm, 2.0 min reaction time). The precision (CV) obtained with the new method is comparable with the standard method. The conditions for the new approach are a first calibration curve, recorded at 505 nm with 800 nm as correction wavelength and 2.8 min reaction time, and a second calibration curve, recorded at 570 nm with 800 nm as correction wavelength and 2.0 min reaction time.

latex coating: 50 mg/g latex) and small latex particles (MP1, approx. 110-140 nm diameter) coated with less affine antibodies (clone 21F12, concentration for latex coating: 45 mg/g latex). Here, the MP2 particles were modified by using larger sizes and antibody loading degrees and the small MP1 particles were modified by using smaller particles, and finally the achievable LDL, UDL and dynamic range determined in the assay as described below.

5.2 Synthesis of the Modified MP2 Particles:

To latex particles (carboxylate-modified microparticles, 290 nm sized) with a concentration of 2% solids in 750 µl MES buffer (20 mM, pH 6.1) 30 µl of a sulfo-NHS (sulfo-N-hydroxysulfosuccinimide, 100 mM in MES buffer) solution and 30 µl of an EDC (1-Ethyl-3-(3-dimethyllaminopropyl)carbodiimide, 100 mM in MES buffer) solution were successively added. The reaction mixture was shortly sonicated and allowed to react for 1 hour at room temperature on a mixing wheel. Afterwards 70 mg antibody 36F12 per gram latex in 750 µl MES buffer (20 mM, pH 6.1) containing 37 µl of Synperonic P85 solution (1% in MES) were mixed with the sulfo-NHS/EDC-activated latex particles. The reaction mixture was shortly sonicated and allowed to react for 2 hours at room temperature on a mixing wheel. To the reaction mixture 45 µl glycine solution (2M, pH 11) were added, sonicated and mixed for 15 minutes on a mixing wheel. Finally the particles were washed 2 times by centrifugation and resuspension in glycine (50 mM, pH 8) containing 0.03% Synperonic P85. After a final centrifugation and resuspension step the latex particles (1% solids) were stored in glycine (50 mM, pH 8) containing 0.03% Synperonic P85, 0.1% BSA and 0.05% sodium azide.

5.3 Synthesis of the Modified MP1 Particles:

To latex particles (carboxylate-modified microparticles, size 90 nm) with a concentration of 2% solids in 750 µl MES

TABLE 5

Result overview for CRP with adapted particles MP2

|  | Standard reagents (MP1: 110-140 nm, 45 mg 21F12/g latex; MP2: 220 nm, 50 mg 36F12/g latex), Standard method (570 nm-800 nm, 2.0 min) | Adapted reagents (MP1: 110-140 nm, 45 mg 21F12/g latex; MP2: 290 nm, 60 mg 36F12/g latex), New method (Cal 1: 505 nm-800 nm, 2.8 min; Cal 2: 570 nm-800 nm, 2.0 min) |
|---|---|---|
| LDL (mg/L) | 0.091 | 0.011 |
| UDL (mg/L) | 350 | 350 |
| Dynamic range | 3846 | 31818 |
| Measuring range (mg/L) | 0.091-350 | 0.011-350 |
| CV at 1 mg/L (%) | 4.6 | 3.4 |
| CV at 5 mg/L (%) | 1.5 | 0.9 |

Example 5: Additional Improvement of the Dynamic Range for the Combination of the Multi-Application Approach with Modified Particles MP1 and MP2

5.1

In addition, the combination of the multi-application approach with adapted particle sizes and antibody loading degrees was assessed using the CRP L3 assay as lead parameter. The CRP L3 assay includes two different types of particles as described in European Patent No. 0 898 169, large latex particles (MP2, approx. 220 nm diameter) coated with highly affine antibodies (clone 36F12; concentration for buffer (20 mM, pH 6.1) 30 µl of a sulfo-NHS (sulfo-N-hydroxysulfosuccinimide, 100 mM in MES buffer) solution and 30 µl of an EDC (1-Ethyl-3-(3-dimethyllaminopropyl) carbodiimide, 100 mM in MES buffer) solution were successively added. The reaction mixture was shortly sonicated and allowed to react for 1 hour at room temperature on a mixing wheel. Afterwards 50 mg antibody 21F12 per gram latex in 750 µl MES buffer (20 mM, pH 6.1) were mixed with the sulfo-NHS/EDC-activated latex particles. After 20 minutes 37 µl of Synperonic P85 solution (1% in MES) was added to the mixture. The reaction mixture was shortly sonicated and allowed to react for 100 minutes at room temperature on a mixing wheel. To the reaction mixture 45

µl glycine solution (2M, pH 11) were added, sonicated and mixed for 15 minutes on a mixing wheel. Finally the particles were washed 2 times by centrifugation and resuspension in glycine (50 mM, pH 8) containing 0.03% Synperonic P85. After a final centrifugation and resuspension step the latex particles (1% solids) were stored in glycine (50 mM, pH 8) containing 0.03% Synperonic P85, 0.1% BSA and 0.05% sodium azide.

5.4 Preparation of the Reagents R1 and R2 for the Analyser Assay:

The reagents R1 and R2 are as described in the package insert document from the tests. The R2 reagent is prepared by mixing the MP1 and MP2 particles synthesized in steps a) and b). The reagents is filled in a cobas C pack.

5.5 Instrument:

See Example 1.

5.6 Procedure for the CRP-Assay Using the Standard Approach:

Identical to the procedure of Example 1.2.

5.7 Pipetting Scheme:

Identical to pipetting scheme of Example 1.3.

5.8 Conditions for the Generation of the Calibration Curve:

Identical to Example 1.4.

5.9 Procedure for the CRP-Assay Using the New Approach of the Present Disclosure:

The reagents used for these experiments were prepared as described above and afterwards filled in cobas C packs: R1 (TRIS buffer) and R2 (Latex particles coated with anti-CRP (mouse) in glycine buffer). The procedure described in the package insert from the CRP L3 test was used with exception of the wavelengths and reaction times.

5.10 Pipetting Scheme:

Identical to pipetting scheme of Example 1.3.

5.11 Conditions for the Generation of the Calibration Curve:

The best conditions for both calibration curves were determined as described earlier and the following result was obtained: 546 nm was used as first wavelength, 800 nm as correction wavelength and 7.1 minutes as first reaction time; 660 nm was used as second wavelength, 800 nm as correction wavelength and 0.8 minutes as second reaction time. The assay type was a two-point-end assay as described under Example 1.4. For the first calibration curve the first reading is at measure point 7 and means shortly after the final reagent addition, and the second reading at measure point 50, which corresponds to a reaction time of 7.1 minutes; for the second calibration curve the first reading is at measure point 7 and means shortly after the final reagent addition, and the second reading at measure point 11, which corresponds to a reaction time of 0.8 minutes. For the generation of both calibration curves each 6 standards covering the corresponding concentrations ranges are measured as duplicates with spline as calibration type, which fits the ranges between the data points of the measured calibrators approximated by third degree polynomials so that a smooth calibration curve is obtained. Similar results were obtained when for both calibration curves the 6 standards from the standard method (Cat. No. 11355279) were used.

The first calibration curve is used which is optimized for a low concentration of the specific analyte thereby maximizing the lower detection limit, the second calibration curve is used which is optimized for a high concentration of the specific analyte thereby maximizing the upper detection limit. Either the first calibration curve or the second calibration curve is to be selected for quantification of CRP, depending on the analyte content or corresponding absorbance of the sample to be quantified. For this purpose the signal of the sample is compared with a predetermined threshold value. The threshold value for CRP may be defined as one of the two or both absorbance values in the calibration curves for CRP which correspond to a concentration of 50 mg/L, with other words the absorbance at 546 nm-800 nm for the reaction time of 7.1 minutes ($A[\lambda 1, t1]=A[546$ nm-800 nm, 7.1 minutes]) and/or the absorbance at 660 nm-800 nm for the reaction time of 0.8 minutes ($A[\lambda 2, t2]=$ A[660 nm-800 nm, 0.8 minutes]).

If the optical signal of the sample calculated for 546 nm-800 nm and 7.1 minutes reaction time is below the predetermined threshold value A[546 nm-800 nm, 7.1 minutes] and/or if the optical signal of the sample calculated for 660 nm-800 nm and 0.8 minutes reaction time is below the predetermined threshold value A[660 nm-800 nm, 0.8 minutes], the first calibration curve is used for its quantitation.

If the optical signal of the sample calculated for 546 nm-800 nm and 7.1 minutes reaction time exceeds the predetermined threshold value A [546 nm-800 nm, 7.1 minutes] and/or if the optical signal of the sample calculated for 660 nm-800 nm and 0.8 minutes reaction time exceeds the predetermined threshold value A [660 nm-800 nm, 0.8 minutes], the second calibration curve is used for its quantitation. As result two calibration curves are obtained for covering the measuring range for CRP determination, the first covering analyte concentrations from 0 to 50 mg/L and the second covering the range from 50 mg/L to the UDL.

Results for the CRP-Assay Using the Standard and New Approach of the Present Disclosure:

5.12 Determination of LDL/UDL/CV:

See Example 1.

5.13 Result Overview and Conclusions:

As depicted in FIG. 2 and Table 6, the use of larger MP2 particles (290 nm instead of 220 nm) with higher antibody loading degrees (70 mg 36F12/g latex instead of 50 mg/g) and of smaller MP1 particles (90 nm instead of 110-140 nm; 50 mg 21F12/g latex the for latex conjugation reaction) in combination with the multi-application approach leads to an improvement of the LDL, UDL and dynamic range by a factor of 3.0, 2.3 and 6.9, respectively, compared with the commercial standard CRP L3 assay using the standard conditions (latex reagent with unmodified MP1 and MP2 particles; measurement at one main wavelength at 570 nm, corrected by 800 nm, 2.0 min reaction time). The precision (CV) obtained with the new method is comparable with the standard method. The conditions for the new approach are a first calibration curve, recorded at 546 nm with 800 nm as correction wavelength and 7.1 min reaction time, and a second calibration curve, recorded at 660 nm with 800 nm as correction wavelength and 0.8 min reaction time.

TABLE 6

Result overview for CRP with adapted particles MP1 and MP2

| | Standard reagents (MP1: 110-140 nm, 45 mg 21F12/g latex; MP2: 220 nm, 50 mg 36F12/g latex), Standard method (570 nm-800 nm, 2.0 min) | Adapted reagents (MP1: 90 nm, 50 mg 21F12/g latex; MP2: 290 nm, 70 mg 36F12/g latex), New method (Cal 1: 546 nm-800 nm, 7.1 min; Cal 2: 660 nm-800 nm, 0.8 min) |
|---|---|---|
| LDL (mg/L) | 0.060 | 0.020 |
| UDL (mg/L) | 367 | 844 |
| Dynamic range | 6117 | 42200 |
| Measuring range (mg/L) | 0.060-367 | 0.020-844 |
| CV at 1 mg/L (%) | 8.3 | 2.7 |
| CV at 5 mg/L (%) | 1.9 | 0.9 |
| CV at 10 mg/L (%) | 1.3 | 1.3 |
| CV at 100 mg/L (%) | 1.3 | 1.3 |

Example 6: Determination of the Dynamic Range of Colorimetric Assays: Alanine Aminotransferase (ALTL)

6.1 Instrument:
See Example 1.
6.2 Procedure for the ALTL (Alanine Aminotransferase) Assay Using the Standard Approach:

Roche's Alanine Aminotransferase test (ALTL, Cat. No. 20764957), a colorimetric assay, was selected for this study. The enzyme alanine aminotransferase (ALT) catalyzes the reaction between L-alanine and 2-oxoglutarate. The pyruvate formed is reduced by NADH in a reaction catalyzed by lactate dehydrogenase (LDH) to form L-lactate and $NAD^+$. The rate of NADH oxidation is directly proportional to the catalytic ALT activity, which is measured photometrically. It is determined by measuring the decrease in absorbance.

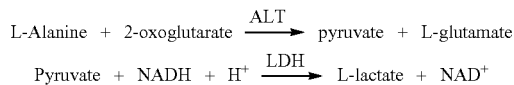

$$\text{L-Alanine} + \text{2-oxoglutarate} \xrightarrow{\text{ALT}} \text{pyruvate} + \text{L-glutamate}$$
$$\text{Pyruvate} + \text{NADH} + \text{H}^+ \xrightarrow{\text{LDH}} \text{L-lactate} + \text{NAD}^+$$

Reagents for all Roche tests are provided in COBAS C packs. These cassettes contain one to three specially designed reagent bottles and have barcode labels with detailed reagent and test-related information. For ALTL tests the cassette is composed of two reagents: R1 (TRIS buffer, pH 7.3, L-alanine, albumin (bovine), LDH (microorganisms), stabilizers and preservative) and R2 (2-Oxoglutarate, NADH, additives and preservative). The procedure described in the package insert of the ALTL test was used as standard method.

6.3 Pipetting Scheme:
9 μL sample and 59 μL assay reagent R1 diluted with 32 μL diluent (water) were subsequently added to the reaction cell, followed by the addition of 17 μl 2-Oxoglutarate and NADH reagent (R2) diluted with 20 μL diluent (water). Afterwards all reaction components were mixed.

6.4 Conditions for the Generation of the Calibration Curve:
Absorbance readings were carried out at 340 nm as main wavelength and at 700 nm as correction wavelength. The assay type was a kinetic A assay, also called rate A assay.

For rate assays, the time course of the reaction is followed by measuring the absorbance as a function of time. That is, measurements are taken as the reaction proceeds. Rate assays use these measurements because their concentration calculations are based on the determination of the rate of change in absorbance. A rate A assay is programmed for multiple measure points. This means, there is a measuring window and every photometric measurement within this window is taken into account for the rate calculation—beginning with the reading at the first programmed measure point through the reading at the second programmed measure point. The absorbance values are converted into the rate of change in absorbance by least squares analysis. For ALTL the first programmed measure point (initial measure point) was measure point 12 which means shortly after the sample and the final reagent were pipetted into the reaction cell (66 seconds after the final reagent addition). The second programmed measure point (final measure point) was taken at measure point 31 which corresponds to a reaction time of 4.1 minutes. The signal was calculated from every reading between the initial and the final measure points. The rate of change in absorbance (slope) between these two measure points was calculated by least squares method. For the generation of the calibration curve two standards from Roche (standard 1: water for the blank measurement; standard 2, Cat. No. 10759350) were measured as duplicates with linear calibration type, which fits the data points of the measured calibrators by a linear mode so that a linear calibration curve is obtained.

6.5 Procedure for the ALTL Assay According to the Invention:
The reagents used for these experiments were identical to those used for the standard method as described in Example 6.2. The procedure described in the package insert from the ALTL test was used with exception of the wavelengths and reaction times.

6.6 Pipetting Scheme:
Identical to the pipetting scheme 6.3.

6.7 Conditions for the Generation of the Calibration Curve:
For the generation of the two calibration curves 2 standards were measured as duplicates with linear as calibration type, which fits the data points of the measured calibrators by a linear mode so that a linear calibration curve was obtained (standard 1: water for the blank measurement; standard 2: from Roche Cat. No. 10759350). The best conditions for both calibration curves were determined as described earlier and the following result was obtained: 340 nm was used as first wavelength, 800 nm as correction wavelength and 8.5 minutes as first reaction time; 376 nm was used as second wavelength, 700 nm as correction wavelength and 1.4 minutes as second reaction time. The assay type was a two-point-end assay for both, the first and second calibration curves as described under Example 1.4. For the first calibration curve the first reading was at measure point 7 and means shortly after the final reagent addition, and the second reading at measure point 57, which corresponds to a reaction time of 8.5 minutes; for the second calibration curve the first reading was at measure point 7 and means shortly after the final reagent addition, and the second reading at measure point 14, which corresponds to a reaction time of 1.4 minutes. Similar results were obtained when using other assay types, such as kinetic A, for the calculation of the first and/or second calibration curves. Furthermore, similar results were achieved when using other standard concentrations than those used here (commercially available calibrators from Roche, Cat. No. 10759350), as well as when using more than 2 standards, e.g., up to six standards for the generation of each calibration curve, and different calibration types for each of the two calibration curves (e.g., spline).

The first calibration curve is used which is optimized for a low concentration of the specific analyte thereby maximizing the lower detection limit, the second calibration curve is used which is optimized for a high concentration of the specific analyte thereby maximizing the upper detection limit. Either the first calibration curve or the second calibration curve is to be selected for quantification of ALTL, depending on the analyte content or corresponding absorbance of the sample to be quantified. For this purpose the signal of the sample is compared with a predetermined threshold value. The threshold value for ALTL may be defined as one of the two or both absorbance values in the calibration curves for ALTL which correspond to a concentration of 200 U/L, with other words the absorbance at 340 nm-800 nm for the reaction time of 8.5 minutes (A[$\lambda$1,t1]= A[340 nm-800 nm, 8.5 minutes]) and/or the absorbance at 376 nm-700 nm for the reaction time of 1.4 minutes (A[$\lambda$2, t2]=A[376 nm-700 nm, 1.4 minutes]).

If the optical signal of the sample calculated for 340 nm-800 nm and 8.5 minutes reaction time is below the predetermined threshold value A[340 nm-800 nm, 8.5 minutes] and/or if the optical signal of the sample calculated for 376 nm-700 nm and 1.4 minutes reaction time is below the predetermined threshold value A[376 nm-700 nm, 1.4 minutes], the second calibration curve is used for its quantitation.

If the optical signal of the sample calculated for 340 nm-800 nm and 8.5 minutes reaction time exceeds the predetermined threshold value A[340 nm-800 nm, 8.5 minutes] and/or if the optical signal of the sample calculated for 376 nm-700 nm and 1.4 minutes reaction time exceeds the predetermined threshold value A[376 nm-700 nm, 1.4 minutes], the first calibration curve is used for its quantitation. As result two calibration curves are obtained for covering the measuring range for ALTL determination, the first covering analyte concentrations from 0 to 200 U/L and the second covering the range from 200 U/L to the UDL.

Results for the ALTL Assay Using the Standard and the Approach According to the Present Disclosure:

6.8 Determination of LDL/UDL/CV:
See Example 1.

6.9 Result Overview and Conclusions:
The result overview is depicted in Table 7. The application of the new approach to Roche's ALTL test shows an increase of the sensitivity (LDL, lower detection limit) by a factor of 2.9 and an extension of the upper detection limit UDL by a factor of 4.2. Finally the dynamic range was extended by a factor of 12.2. The precision (CV) obtained with the new method is comparable with the standard method. The new approach affords minimal implementation; the application of the approach does not need any changes of reagents and their formulations. Only the number and/or concentration of standards for the calibration may be adapted if needed.

TABLE 7

Result overview for ALTL

| | Standard method (340 nm wavelength, 700 nm correction wavelength, 4.1 min. reaction time) | New method (calibration curve 1: 340 nm wavelength, 800 nm correction wavelength, 8.5 min. reaction time; calibration curve 2: 376 nm wavelength, 700 nm correction wavelength, 1.4 min reaction time) |
|---|---|---|
| LDL (U/L) | 1.6 | 0.55 |
| UDL (U/L) | 811 | 3383 |
| Dynamic range | 507 | 6151 |
| Measuring range (U/L) | 1.6-811 | 0.55-3383 |
| CV at 10 U/L (%) | 8.37 | 5.00 |
| CV at 150 U/L (%) | 0.53 | 0.30 |
| CV at 2000 U/L (%) | 0.47 | 0.44 |

Example 7: Determination of the Dynamic Range of Colorimetric Assays: Aspartate Aminotransferase (ASTL)

7.1 Instrument:
See Example 1.

7.2 Procedure for the ASTL (Aspartate Aminotransferase) Assay Using the Standard Approach:
Roche's Aspartate Aminotransferase test (ASTL, Cat. No. 20764949), a colorimetric assay, was selected for this study. The enzyme aspartate aminotransferase (AST) catalyzes the reaction between L-aspartate and 2-oxoglutarate. The oxalacetate formed is reduced by NADH in a reaction catalyzed by malate dehydrogenase (MDH) to form L-malate and NAD$^+$. The rate of NADH oxidation is directly proportional to the catalytic AST activity which is measured photometrically. It is determined by measuring the decrease in absorbance.

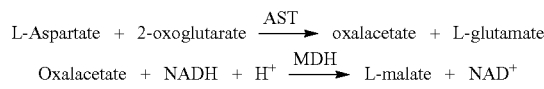

Reagents for all Roche tests are provided in cobas c packs. These cassettes contain one to three specially designed reagent bottles and have barcode labels with detailed reagent and test-related information. For ASTL tests the cassette is composed of two reagents: R1 (TRIS buffer, pH 7.8, L-aspartate, albumin (bovine), MDH (microorganisms), LDH (microorganisms), stabilizers and preservative) and R2 (2-Oxoglutarate, NADH and preservative). The procedure described in the package insert of the ASTL test was used as standard method.

7.3 Pipetting Scheme:

9 μL sample and 40 μL assay reagent R1 diluted with 51 μL diluent (water) were subsequently added to the reaction cell, followed by the addition of 17 μl reagent R2 diluted with 20 diluent (water). Afterwards the reaction mixture was mixed.

7.4 Conditions for the Generation of the Calibration Curve:

Absorbance readings were carried out at 340 nm as main wavelength and at 700 nm as correction wavelength. The assay type was a kinetic A assay, also called rate A assay.

For rate assays, the time course of the reaction is followed by measuring the absorbance as a function of time. That is, measurements are taken as the reaction proceeds. Rate assays use these measurements because their concentration calculations are based on the determination of the rate of change in absorbance. A rate A assay is programmed for multiple measure points. This means, there is a measuring window and every photometric measurement within this window is taken into account for the rate calculation—beginning with the reading at the first programmed measure point through the reading at the second programmed measure point. The absorbance values are converted into the rate of change in absorbance by least squares analysis. For ALTL the first programmed measure point (initial measure point) was measure point 12, which means shortly after the sample and the final reagent were pipetted into the reaction cell (66 seconds after the final reagent addition). The second programmed measure point (final measure point) was taken at measure point 31 which corresponds to a reaction time of 4.1 minutes. The signal was calculated from every reading between the initial and the final measure points. The rate of change in absorbance (slope) between these two measure points was calculated by least squares method. For the generation of the calibration curve two standards from Roche (standard 1: water for the blank measurement; standard 2, Cat. No. 10759350) were measured as duplicates with linear calibration type, which fits the data points of the measured calibrators by a linear mode so that a linear calibration curve is obtained.

7.5 Procedure for the ASTL Assay According to the Present Disclosure:

The reagents used for these experiments were identical to those used for the standard method as described in Example 7.2. The procedure described in the package insert from the ASTL test was used with exception of the wavelengths and reaction times.

7.6 Pipetting Scheme:

Identical to the pipetting scheme 7.3.

7.7 Conditions for the Generation of the Calibration Curve:

For the generation of the two calibration curves 2 standards were measured as duplicates with linear as calibration type, which fits the data points of the measured calibrators by a linear mode so that a linear calibration curve was obtained (standard 1: water for the blank measurement; standard 2: from Roche Cat. No. 10759350). The best conditions for both calibration curves were determined as described earlier and the following result was obtained: 340 nm was used as first wavelength, 700 nm as correction wavelength and 8.3 minutes as first reaction time; 376 nm was used as second wavelength, 800 nm as correction wavelength and 1.2 minutes as second reaction time. The assay type was a two-point-end assay for both, the first and second calibration curves as described under Example 1.4. For the first calibration curve the first reading was at measure point 8 and means shortly after the final reagent addition, and the second reading at measure point 57, which corresponds to a reaction time of 8.3 minutes; for the second calibration curve the first reading was at measure point 8 and means shortly after the final reagent addition, and the second reading at measure point 14, which corresponds to a reaction time of 1.2 minutes. Similar results were obtained when using other assay types, such as kinetic A, for the calculation of the first and/or second calibration curves. Furthermore, similar results were achieved when using other standard concentrations than those used here (commercially available calibrators from Roche, Cat. No. 10759350), as well as when using more than 2 standards, e.g., up to six standards for the generation of each calibration curve, and different calibration types for each of the two calibration curves (e.g., spline).

The first calibration curve is used which is optimized for a low concentration of the specific analyte thereby maximizing the lower detection limit, the second calibration curve is used which is optimized for a high concentration of the specific analyte thereby maximizing the upper detection limit. Either the first calibration curve or the second calibration curve is to be selected for quantification of ASTL, depending on the analyte content or corresponding absorbance of the sample to be quantified. For this purpose the signal of the sample is compared with a predetermined threshold value. The threshold value for ASTL may be defined as one of the two or both absorbance values in the calibration curves for ASTL, which correspond to a concentration of 200 U/L, with other words the absorbance at 340 nm-700 nm for the reaction time of 8.3 minutes ($A[\lambda 1, t1]$ = $A[340 nm-700 nm, 8.3 minutes]$) and/or the absorbance at 376 nm-800 nm for the reaction time of 1.2 minutes ($A[\lambda 2, t2]$=$A[376 nm-800 nm, 1.2 minutes]$).

If the optical signal of the sample calculated for 340 nm-700 nm and 8.3 minutes reaction time is below the predetermined threshold value A[340 nm-700 nm, 8.3 minutes] and/or if the optical signal of the sample calculated for 376 nm-800 nm and 1.2 minutes reaction time is below the predetermined threshold value A[376 nm-800 nm, 1.2 minutes], the second calibration curve is used for its quantitation.

If the optical signal of the sample calculated for 340 nm-700 nm and 8.3 minutes reaction time exceeds the predetermined threshold value A[340 nm-700 nm, 8.3 minutes] and/or if the optical signal of the sample calculated for 376 nm-800 nm and 1.2 minutes reaction time exceeds the predetermined threshold value A[376 nm-800 nm, 1.2 minutes], the first calibration curve is used for its quantitation. As result two calibration curves are obtained for covering the measuring range for ASTL determination, the first covering analyte concentrations from 0 to 200 U/L and the second covering the range from 200 U/L to the UDL.

Results for the ASTL Assay Using the Standard and the Approach According to the Invention:

7.8 Determination of LDL/UDL/CV:

See Example 1.

7.9 Result Overview and Conclusions:

The result overview is depicted in Table 8. The application of the new approach to Roche's ASTL test shows an increase of the sensitivity (LDL, lower detection limit) by a factor of 2.2 and an extension of the upper detection limit UDL by a factor of 3.4. Finally, the dynamic range was extended by a factor of 7.5. The precision (CV) obtained with the new method is comparable with the standard method. The new approach affords minimal implementation; the application of the approach does not need any changes of reagents and their formulations. Only the number and/or concentration of standards for the calibration may be adapted if needed.

TABLE 8

Result overview for ASTL

|  | Standard method (340 nm wavelength, 700 nm correction wavelength, 4.1 min. reaction time) | New method (calibration curve 1: 340 nm wavelength, 700 nm correction wavelength, 8.3 min. reaction time; calibration curve 2: 376 nm wavelength, 800 nm correction wavelength, 1.2 min reaction time) |
|---|---|---|
| LDL (U/L) | 1.71 | 0.78 |
| UDL (U/L) | 854 | 2868 |
| Dynamic range | 502 | 3677 |
| Measuring range (U/L) | 1.71-854 | 0.78-2868 |
| CV at 20 U/L (%) | 4.46 | 1.67 |
| CV at 150 U/L (%) | 0.58 | 0.27 |
| CV at 2000 U/L (%) | 1.12 | 0.31 |

Example 8: Determination of the Dynamic Range of Colorimetric Assays: Blood-Urea-Nitrogen (U-BUN)

8.1 Instrument:

See Example 1.

8.2 Procedure for the U-BUN (Blood-Urea-Nitrogen) Assay Using the Standard Approach:

Roche's Blood-Urea-Nitrogen test (UREAL, Cat. No. 04460715), a colorimetric assay, was selected for this study. The enzyme urease hydrolyzes urea in the presence of urease to form ammonium and carbonate. In the following reaction glutamate dehydrogenase (GLDH) catalyzes the reaction between 2-oxoglutarate, ammonium and NADH resulting in L-glutamate and $NAD^+$ formation. The rate of decrease in the NADH concentration is directly proportional to the urea concentration in the specimen and is measured photometrically. It is determined by measuring the decrease in absorbance.

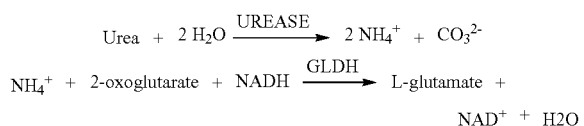

Reagents for all Roche tests are provided in COBAS C packs. These cassettes contain one to three specially designed reagent bottles and have barcode labels with detailed reagent and test-related information. For U-BUN tests the cassette is composed of two reagents: R1 (NaCl 9%) and R2 (TRIS buffer, pH 8.6, 2-oxoglutarate, NADH, ADP, urease (jack bean), GLDH (bovine liver), nonreactive stabilizers and preservatives). The procedure described in the package insert of the U-BUN (UREAL) test was used as standard method.

8.3 Pipetting Scheme:

2 μL sample and 10 μL assay reagent R1 diluted with 90 μL diluent (water) were subsequently added to the reaction cell, followed by the addition of 38 μl of reagent R2 diluted with 110 μL diluent (water). Afterwards the reaction components were mixed.

8.4 Conditions for the Generation of the Calibration Curve:

Absorbance readings were carried out at 340 nm as main wavelength and at 700 nm as correction wavelength. The assay type was a kinetic A assay, also called rate A assay.

For rate assays, the time course of the reaction is followed by measuring the absorbance as a function of time. That is, measurements are taken as the reaction proceeds. Rate assays use these measurements because their concentration calculations are based on the determination of the rate of change in absorbance. A rate A assay is programmed for multiple measure points. This means, there is a measuring window and every photometric measurement within this window is taken into account for the rate calculation—beginning with the reading at the first programmed measure point through the reading at the second programmed measure point. The absorbance values are converted into the rate of change in absorbance by least squares analysis. For U-BUN the first programmed measure point (initial measure point) was measure point 10 which means shortly after the sample and the final reagent were pipetted into the reaction cell (42 seconds after the final reagent addition). The second programmed measure point (final measure point) was taken at measure point 19 which corresponds to a reaction time of 1.8 minutes. The signal was calculated from every reading between the initial and the final measure points. The rate of change in absorbance (slope) between these two measure points was calculated by least squares method. For the generation of the calibration curve two standards from Roche (standard 1: water for the blank measurement; standard 2, Cat. No. 10759350) were measured as duplicates with linear calibration type, which fits the data points of the measured calibrators by a linear mode so that a linear calibration curve is obtained.

8.5 Procedure for the U-BUN Assay According to the Present Disclosure:

The reagents used for these experiments were identical to those used for the standard method as described in Example 8.2. The procedure described in the package insert of the U-BUN (UREAL) test was used with exception of the wavelengths and reaction times.

8.6 Pipetting Scheme:
Identical to the pipetting scheme 8.3.
8.7 Conditions for the Generation of the Calibration Curve:
For the generation of the two calibration curves 2 standards were measured as duplicates with linear as calibration type, which fits the data points of the measured calibrators by a linear mode so that a linear calibration curve was obtained (standard 1: water for the blank measurement; standard 2: from Roche Cat. No. 10759350). The best conditions for both calibration curves were determined as described earlier and the following result was obtained: for the first calibration curve 340 nm was used as first wavelength, 800 nm as correction wavelength and 8.3 minutes as first reaction time; for the second calibration curve 376 nm was used as second wavelength, 700 nm as correction wavelength and 1.4 minutes as second reaction time. The assay type was a two-point-end assay for both, the first and second calibration curves as described under Example 1.4. For the first calibration curve the first reading was at measure point 8 and means shortly after the final reagent addition, and the second reading at measure point 57, which corresponds to a reaction time of 8.3 minutes; for the second calibration curve the first reading was at measure point 8 and means shortly after the final reagent addition, and the second reading at measure point 15, which corresponds to a reaction time of 1.4 minutes. Similar results were obtained when using other assay types, such as kinetic A, for the calculation of the first and/or second calibration curves. Furthermore, similar results were achieved when using other standard concentrations than those used here (commercially available calibrators from Roche, Cat. No. 10759350), as well as when using more than 2 standards, e.g., up to six standards for the generation of each calibration curve, and different calibration types for each of the two calibration curves (e.g., spline).

The first calibration curve is used which is optimized for a low concentration of the specific analyte thereby maximizing the lower detection limit, the second calibration curve is used which is optimized for a high concentration of the specific analyte thereby maximizing the upper detection limit. Either the first calibration curve or the second calibration curve is to be selected for quantification of U-BUN, depending on the analyte content or corresponding absorbance of the sample to be quantified. For this purpose the signal of the sample is compared with a predetermined threshold value. The threshold value for U-BUN may be defined as one of the two or both absorbance values in the calibration curves for U-BUN which correspond to a concentration of 10 mmol/L, with other words the absorbance at 340 nm-800 nm for the reaction time of 8.3 minutes (A[$\lambda$1, t1]=A[340 nm-800 nm, 8.3 minutes]) and/or the absorbance at 376 nm-700 nm for the reaction time of 1.4 minutes (A[$\lambda$2,t2]=A[376 nm-700 nm, 1.4 minutes]).

If the optical signal of the sample calculated for 340 nm-800 nm and 8.3 minutes reaction time is below the predetermined threshold value A[340 nm-800 nm, 8.3 minutes] and/or if the optical signal of the sample calculated for 376 nm-700 nm and 1.4 minutes reaction time is below the predetermined threshold value A[376 nm-700 nm, 1.4 minutes, the second calibration curve is used for its quantitation.

If the optical signal of the sample calculated for 340 nm-800 nm and 8.3 minutes reaction time exceeds the predetermined threshold value A[340 nm-800 nm, 8.3 minutes] and/or if the optical signal of the sample calculated for 376 nm-700 nm and 1.4 minutes reaction time exceeds the predetermined threshold value A[376 nm-700 nm, 1.4 minutes], the first calibration curve is used for its quantitation. As result two calibration curves are obtained for covering the measuring range for U-BUN determination, the first covering analyte concentrations from 0 to 10 mmol/L and the second covering the range from 10 mmol/L to the UDL. Results for the U-BUN (UREAL) Assay Using the Standard and the Approach According to the Present Disclosure:
8.8 Determination of LDL/UDL/CV:
See Example 1.
8.9 Result Overview and Conclusions:
The result overview is depicted in Table 9. The application of the new approach to Roche's U-BUN test shows an increase of the sensitivity (LDL, lower detection limit) by a factor of 2.2 and an extension of the upper detection limit UDL by a factor of 1.4. Finally the dynamic range was extended by a factor of 3. The precision (CV) obtained with the new method is comparable with the standard method. The new approach affords minimal implementation; the application of the approach does not need any changes of reagents and their formulations. Only the number and/or concentration of standards for the calibration may be adapted if needed.

TABLE 9

Result overview for U-BUN

| | Standard method (340 nm wavelength, 700 nm correction wavelength, 1.8 min. reaction time) | New method (calibration curve 1: 340 nm wavelength, 800 nm correction wavelength, 8.3 min. reaction time; calibration curve 2: 376 nm wavelength, 700 nm correction wavelength, 1.4 min reaction time) |
|---|---|---|
| LDL (mmol/L) | 0.071 | 0.032 |
| UDL (mmol/L) | 57 | 78 |
| Dynamic range | 803 | 2438 |
| Measuring range (mmol/L) | 0.071-57 | 0.032-78 |
| CV at 2 mmol/L (%) | 1.74 | 1.35 |
| CV at 10 mmol/L (%) | 0.99 | 0.91 |
| CV at 60 mmol/L (%) | 0.72 | 0.92 |

Example 9: Determination of the Dynamic Range of Colorimetric Assays: Glucose (Gluc3)

9.1 Instrument:
See Example 1.
9.2 Procedure for the Glucose (Gluc3) Assay Using the Standard Approach:
Roche's Glucose test (Gluc3, Cat. No. 04404483), a colorimetric assay, was selected for this study. The enzyme hexokinase catalyzes the phosphorylation of glucose to glucose-6-phosphate (G-6-P) by ATP. In the following reaction glucose-6-phosphate dehydrogenase (G-6-PDH) oxidizes glucose-6-phosphate in presence of NADP+ resulting in gluconate-6-phosphate and NADPH formation. The rate of NADPH formation is directly proportional to the glucose concentration in the specimen and is measured photometrically. It is determined by measuring the increase in absorbance.

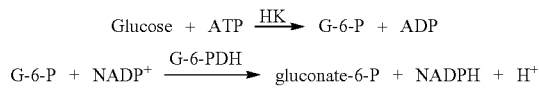

Reagents for all Roche tests are provided in COBAS C packs. These cassettes contain one to three specially designed reagent bottles and have barcode labels with detailed reagent and test-related information. For Gluc3 tests the cassette is composed of two reagents: R1 (MES buffer, pH 6.0, $Mg^{2+}$, ATP, NADP and preservative) and R2 (HEPES buffer, pH 8.0, $Mg^{2+}$, hexokinase (yeast), glucose-6-phosphate dehydrogenase (*E. coli*) and preservatives). The procedure described in the package insert of the Gluc3 test was used as standard method.

9.3 Pipetting Scheme:

2 μL sample and 28 μL assay reagent R1 diluted with 141 μL diluent (water) were subsequently added to the reaction cell, followed by the addition of 10 μl of reagent R2 diluted with 200 μL diluent (water). Afterwards the reaction components were mixed.

9.4 Conditions for the Generation of the Calibration Curve:

Absorbance readings were carried out at 340 nm as main wavelength and at 700 nm as correction wavelength. The absorbance readings were performed at two different measure points. The assay type was a two-point-end assay. A two-point-end assay is an end-point-assay which performs a sample blank. Here two absorbance readings at two different measure points are considered: the first reading is usually taken before or shortly after the final reagent is added; the second reading is taken at any time point after the final reagent was added. The absorbance value for the calibration curve and therefore for the concentration calculation is obtained by subtraction of the first reading from the second reading.

For Gluc3 the first reading is at measure point 6 and means shortly before the final reagent addition, and the second reading at measure point 32, which corresponds to a reaction time of 5.5 minutes. For the generation of the calibration curve two standards were measured as duplicates with linear as calibration type, which fits the data points of the measured calibrators by a linear mode so that a linear calibration curve is obtained (standard 1: water for the blank measurement; standard 2: from Roche Cat. No. 10759350).

9.5 Procedure for the Gluc3 Assay According to the Invention:

The reagents used for these experiments were identical to those used for the standard method as described in Example 9.2. The procedure described in the package insert of the Gluc3 test was used with exception of the wavelengths and reaction times.

9.6 Pipetting Scheme:

Identical to the pipetting scheme 9.3.

9.7 Conditions for the Generation of the Calibration Curve:

For the generation of the two calibration curves two standards were measured as duplicates with linear as calibration type, which fits the data points of the measured calibrators by a linear mode so that a linear calibration curve was obtained (standard 1: water for the blank measurement; standard 2: from Roche Cat. No. 10759350). The best conditions for both calibration curves were determined as described earlier and the following result was obtained: for the first calibration curve 340 nm was used as first wavelength, 700 nm as correction wavelength and 8.7 minutes as first reaction time; for the second calibration curve 376 nm was used as second wavelength, 700 nm as correction wavelength and 5.5 minutes as second reaction time. The assay type was a two-point-end assay which was already described in the standard method for Gluc3 test. For the first calibration curve the first reading was performed at measure point 6 (6 seconds before the final reagent addition) and the second reading at measure point 57, which corresponds to a reaction time of 8.7 minutes; for the second calibration curve the first reading was also at measure point 6 and the second reading at measure point 32, which corresponds to a reaction time of 5.5 minutes. Similar results were obtained when using other assay types, such as kinetic A, for the calculation of the first and/or second calibration curves. Furthermore, similar results were achieved when using other standard concentrations than those used here (commercially available calibrators from Roche, Cat. No. 10759350), as well as when using more than 2 standards, e.g., up to six standards for the generation of each calibration curve, and different calibration types for each of the two calibration curves (e.g., spline).

The first calibration curve is used which is optimized for a low concentration of the specific analyte thereby maximizing the lower detection limit, the second calibration curve is used which is optimized for a high concentration of the specific analyte thereby maximizing the upper detection limit. Either the first calibration curve or the second calibration curve is to be selected for quantification of Gluc3, depending on the analyte content or corresponding absorbance of the sample to be quantified. For this purpose the signal of the sample is compared with a predetermined threshold value. The threshold value for Gluc3 may be defined as one of the two or both absorbance values in the calibration curves for Gluc3 which correspond to a concentration of 10 mmol/L, with other words the absorbance at 340 nm-700 nm for the reaction time of 8.7 minutes ($A[\lambda 1, t1]=A[340\ nm-700\ nm, 8.7\ minutes]$) and/or the absorbance at 376 nm-700 nm for the reaction time of 5.5 minutes ($A[\lambda 2, t2]=A[376\ nm-700\ nm, 5.5\ minutes]$).

If the optical signal of the sample calculated for 340 nm-700 nm and 8.7 minutes reaction time is below the predetermined threshold value A[340 nm-700 nm, 8.7 minutes] and/or if the optical signal of the sample calculated for 376 nm-700 nm and 5.5 minutes reaction time is below the predetermined threshold value A[376 nm-700 nm, 5.5 minutes], the first calibration curve is used for its quantitation.

If the optical signal of the sample calculated for 340 nm-700 nm and 8.7 minutes reaction time exceeds the predetermined threshold value A[340 nm-700 nm, 8.7 minutes] and/or if the optical signal of the sample calculated for 376 nm-700 nm and 5.5 minutes reaction time exceeds the predetermined threshold value A[376 nm-700 nm, 5.5 minutes], the second calibration curve is used for its quantitation. As result two calibration curves are obtained for covering the measuring range for Gluc3 determination, the first covering analyte concentrations from 0 to 10 mmol/L and the second covering the range from 10 mmol/L to the UDL.

Results for the Gluc3 Assay Using the Standard and the Approach According to the Invention:

9.8 Determination of LDL/UDL/CV:
See Example 1.

9.9 Result Overview and Conclusions:

The result overview is depicted in Table 10. The application of the new approach to Roche's Gluc3 test shows an increase of the sensitivity (LDL, lower detection limit) by a factor of 1.5 and an extension of the upper detection limit UDL by a factor of 1.6. Finally the dynamic range was extended by a factor of 2.4. The precision (CV) obtained with the new method is comparable with the standard method. The new approach affords minimal implementation; the application of the approach does not need any changes of reagents and their formulations. Only the number and/or concentration of standards for the calibration may be adapted if needed.

TABLE 10

Result overview for Gluc3

|  | Standard method (340 nm wavelength, 700 nm correction wavelength, 5.5 min. reaction time) | New method (calibration curve 1: 340 nm wavelength, 700 nm correction wavelength, 8.7 min. reaction time; calibration curve 2: 376 nm wavelength, 700 nm correction wavelength, 5.5 min reaction time) |
|---|---|---|
| LDL (mmol/L) | 0.017 | 0.011 |
| UDL (mmol/L) | 46 | 73 |
| Dynamic range | 2706 | 6636 |
| Measuring range (mmol/L) | 0.017-46 | 0.011-73 |
| CV at 0.3 mmol/L (%) | 6.51 | 5.94 |
| CV at 10 mmol/L (%) | 0.75 | 0.71 |
| CV at 100 mmol/L (%) | 0.55 | 0.83 |

It is noted that terms like "preferably", "commonly", and "typically" are not utilized herein to limit the scope of the claimed subject matter or to imply that certain features are critical, essential, or even important to the structure or function of the embodiments disclosed herein. Rather, these terms are merely intended to highlight alternative or additional features that may or may not be utilized in a particular embodiment of the present invention.

It is also noted that the terms "substantially" and "about" may be utilized herein to represent the inherent degree of uncertainty that may be attributed to any quantitative comparison, value measurement, or other representation. These terms are also utilized herein to represent the degree by which a quantitative representation may vary from a stated reference without resulting in a change in the basic function of the subject matter at hand.

It will be apparent to those skilled in the art that various modifications and variations can be made to the embodiments described herein without departing from the spirit and scope of the claimed subject matter. Thus, it is intended that the specification cover the modifications and variations of the various embodiments described herein, provided such modifications and variations come within the scope of the appended claims and their equivalents.

What is claimed is:

1. A method for determining the amount of a specific analyte by photometric assays across a wide range using a spectrophotometer, wherein the specific analyte in a sample reacts with an analyte specific reaction partner in a reaction mixture, comprising the steps of:

a) generating at least two calibration curves, wherein
  the first calibration curve recorded at a first wavelength is optimized for low concentrations of the specific analyte thereby maximizing the lower detection limit, and
  the second calibration curve recorded at a second wavelength is optimized for high concentrations of the specific analyte thereby maximizing the upper detection limit;
b) irradiating the reaction mixture using the spectrophotometer with light concentrated at at least the first and second wavelengths and measuring simultaneously the optical signal for the specific analyte of a sample to be determined in the reaction mixture at least at the first and second wavelengths using the spectrophotometer;
c) selecting either the first or the second calibration curve for quantification of the specific analyte, by the following criteria:
  for increasing calibration curves:
    if the optical signal of the first and/or the second wavelength is lower than a corresponding predetermined threshold value, the concentration of the analyte is determined by the use of the first calibration curve recorded at the first wavelength;
    if the optical signal of the first and/or the second wavelength exceeds a corresponding predetermined threshold value, the concentration of the analyte is determined by the use of the second calibration curve recorded at the second wavelength;
  for decreasing calibration curves:
    if the optical signal of the first and/or the second wavelength is lower than a corresponding predetermined threshold value, the concentration of the analyte is determined by the use of the second calibration curve recorded at the second wavelength;
    if the optical signal of the first and/or the second wavelength exceeds a corresponding predetermined threshold value, the concentration of the analyte is determined by the use of the first calibration curve recorded at the first wavelength, and
d) quantifying the amount of the specific analyte by comparison with the selected calibration curve.

2. The method according to claim 1, wherein in turbidimetric and nephelometric immunoassays the specific analyte is quantified from the change in the turbidity of the reaction mixture based on the agglutination of the specific analyte and an analyte specific binding partner.

3. The method according to claim 1, wherein in colorimetric assays the specific analyte is quantified with the aid of a color reagent.

4. The method according to claim 1, wherein the first calibration curve is recorded at a first wavelength and at a first reaction time.

5. The method according to claim 1, wherein the second calibration curve is recorded at a second wavelength and of a second reaction time.

6. The method according to claim 1, wherein the simultaneous measurement of the optical signal for the specific analyte of a sample to be determined in the reaction mixture is performed at least at the first and second wavelengths over the complete reaction time.

7. The method according to claim 1, wherein the measurement results are stored in a data management system of the instrument platform.

8. The method according to claim 1, wherein further wavelengths are determined as a blank value for the correction of interferences and compensation of photometric noise.

9. The method according to claim 1, wherein at least two calibration curves are generated that are recorded at the same wavelengths and at different reaction times.

10. The method according to claim 1, wherein the analyte specific reaction partner further comprises binding proteins, antigens, antigen fragments, antibodies, antibody fragments, nucleic acids, receptors and particle enhanced binding partners, enzymes, substrates or specific chemical reagents leading to a color change or to a turbidity change in the presence of an analyte.

11. A computer-implemented method of determining the optimal wavelength, reaction time and threshold according to claim 1, comprising the steps of:
  a) receiving a dataset representing the absorbance values of the samples recorded at multiple wavelengths over the complete reaction time simultaneously available on an analyzer, wherein said dataset includes a plurality of data points for:
    standards for the calibration,
    a blank sample for determination of lower detection limit,
    at least 2 samples for the determination of the precision, and/or
    dilution series;
  b) setting the threshold values at a concentration where the calibration curves change from the first to the second calibration curve, by using for lower concentrations the first calibration curve for the analyte quantification and by using for higher concentrations the second calibration curve for the analyte quantification; and
  c) determining the first and second wavelength as well as the first and the second reaction time, analyzing the kinetic curves and selecting the optimal set up for the first calibration curve and the second calibration curve.

12. The method of claim 1 in which the first wavelength is different from the second wavelength.

13. A method for increasing the sensitivity and/or dynamic range of photometric assays using a spectrophotometer, wherein the specific analyte in a sample reacts with an analyte specific reaction partner in a reaction mixture, comprising the steps of:
  a) generating at least two calibration curves, wherein
    the first calibration curve recorded at a first wavelength is optimized for low concentrations of the specific analyte thereby maximizing the lower detection limit, and
    the second calibration curve recorded at a second wavelength is optimized for high concentrations of the specific analyte thereby maximizing the upper detection limit;
  b) irradiating the reaction mixture using the spectrophotometer with light concentrated at at least the first and second wavelengths and measuring simultaneously the optical signal for the specific analyte of a sample to be determined in the reaction mixture at least at the first and second wavelengths using the spectrophotometer;
  c) selecting either the first or the second calibration curve for quantification of the specific analyte, by the following criteria:
    for increasing calibration curves:
      if the optical signal of the first and/or the second wavelength is lower than a corresponding predetermined threshold value, the concentration of the analyte is determined by the use of the first calibration curve recorded at the first wavelength,
      if the optical signal of the first and/or the second wavelength exceeds a corresponding predetermined threshold value, the concentration of the analyte is determined by the use of the second calibration curve recorded at the second wavelength;
    for decreasing calibration curves:
      if the optical signal of the first and/or the second wavelength is lower than a corresponding predetermined threshold value, the concentration of the analyte is determined by the use of the second calibration curve recorded at the second wavelength,
      if the optical signal of the first and/or the second wavelength exceeds a corresponding predetermined threshold value, the concentration of the analyte is determined by the use of the first calibration curve recorded at the first wavelength; and
  d) quantifying the amount of the specific analyte by comparison with the selected calibration curve.

14. A computer readable medium including non-transitory code controlling a processor to determine the optimal wavelength, reaction time and threshold according to one of the preceding claims, the code including instructions to:
  a) receiving a dataset representing the absorbance values of the samples recorded at multiple wavelengths over the complete reaction time simultaneously available on an analyzer, wherein said dataset includes a plurality of data points for:
    standards for the calibration,
    a blank sample for determination of lower detection limit,
    at least 2 samples for the determination of the precision, and/or
    dilution series;
  b) setting the threshold values at a concentration where the calibration curves change from the first to the second calibration curve, by using for lower concentrations the first calibration curve for the analyte quantification and by using for higher concentrations the second calibration curve for the analyte quantification; and c) determining the first and second wavelength as well as the first and the second reaction time, analyzing the kinetic curves and selecting the optimal set up for the first calibration curve and the second calibration curve.

15. A method for determining the amount of a specific analyte by photometric assays across a wide range using a spectrophotometer, wherein the specific analyte in a sample reacts with an analyte specific reaction partner in a reaction mixture, comprising the steps of:
   a) irradiating the reaction mixture using the spectrophotometer with light concentrated at at least the first and second wavelengths and measuring simultaneously the optical signal for the specific analyte of a sample to be determined in the reaction mixture at least at a first wavelength and a second wavelength using the spectrophotometer;
   b) selecting either a first calibration curve or a second calibration curve for quantification of the specific analyte, the first calibration curve having been recorded at the first wavelength for use with low concentrations of the specific analyte, and the second calibration curve having been recorded at the second wavelength optimized for use with the specific analyte, said selecting based on the following criteria:
      for increasing calibration curves:
         if the optical signal of the first and/or the second wavelength is lower than a corresponding predetermined threshold value, the concentration of the analyte is determined by the use of the first calibration curve recorded at the first wavelength;
         if the optical signal of the first and/or the second wavelength exceeds a corresponding predetermined threshold value, the concentration of the analyte is determined by the use of the second calibration curve recorded at the second wavelength;
      for decreasing calibration curves:
         if the optical signal of the first and/or the second wavelength is lower than a corresponding predetermined threshold value, the concentration of the analyte is determined by the use of the second calibration curve recorded at the second wavelength;
         if the optical signal of the first and/or the second wavelength exceeds a corresponding predetermined threshold value, the concentration of the analyte is determined by the use of the first calibration curve recorded at the first wavelength, and
   c) quantifying the amount of the specific analyte by comparison with the selected calibration curve.

* * * * *